United States Patent
Yu et al.

(10) Patent No.: US 8,669,054 B2
(45) Date of Patent: Mar. 11, 2014

(54) MARKER FOR GASTRIC CANCER AND METHOD FOR DETECTING GASTRIC CANCER

(75) Inventors: Jun Yu, Lake Silver (CN); Joseph Jao Yiu Sung, Shatin (CN); Xiaoxing Li, Shatin (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 171 days.

(21) Appl. No.: 12/771,672

(22) Filed: Apr. 30, 2010

(65) Prior Publication Data

US 2011/0269123 A1 Nov. 3, 2011

(51) Int. Cl.
  *C12Q 1/68* (2006.01)
(52) U.S. Cl.
  USPC .......................................... 435/6.1
(58) Field of Classification Search
  None
  See application file for complete search history.

(56) References Cited

FOREIGN PATENT DOCUMENTS

WO    WO 2008103761 A2 *  8/2008

OTHER PUBLICATIONS

Kim et al., Annals of Clinical & Laboratory Science, 2003, vol. 33, pp. 32-38.*
Shin et al., Aliment Pharmacol Ther, 2002, vol. 16, pp. 137-144.*
Stedman's Medical Dictionary, Williams and Wilkins, 26th Edition, 1995, p. 1435.*
Palmisano et al., 2003, Cancer Research, vol. 63, 4620-4625.*
Kim et al., 2006, BMC Cancer, vol. 6, p. 1-18.*
Kusano et al., Cancer, 2006, vol. 106, pp. 1467-1479.*

* cited by examiner

*Primary Examiner* — Anne Gussow
*Assistant Examiner* — Mindy G Brown
(74) *Attorney, Agent, or Firm* — Kilpatrick Townsend & Stockton LLP

(57) ABSTRACT

In embodiments the expression or methylation of the PAX5 gene is used as a marker for the diagnosis and prognosis of gastric cancer. In further embodiments methods for detecting gastric cancer are disclosed as are methods for inhibiting the growth of gastric cancer.

11 Claims, 11 Drawing Sheets

MARKER FOR GASTRIC CANCER AND METHOD FOR DETECTING GASTRIC CANCER

FIELD

The subject matter disclosed generally relates to markers for gastric cancer, and methods for detecting gastric cancer.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 87509-14.TXT, created on Aug. 26, 2013, 28,672 bytes, machine format IBM-PC, MS-Windows operating system, is hereby incorporated by reference in its entirety for all purposes.

BACKGROUND

The following prior art publications are noted:
Busslinger, M., Klix, N., Pfeffer, P., Graninger, P. G., & Kozmik, Z. (1996). Deregulation of PAX-5 by translocation of the Emu enhancer of the IgH locus adjacent to two alternative PAX-5 promoters in a diffuse large-cell lymphoma. Proc Natl Acad Sci USA, 93(12), 6129-6134.
Livak, K. J., & Schmittgen, T. D. (2001). Analysis of relative gene expression data using real-time quantitative PCR and the 2(-Delta Delta C(T)) Method. Methods, 25(4), 402-408.
Takai, D., & Jones, P. A. (2002). Comprehensive analysis of CpG islands in human chromosomes 21 and 22. Proc Natl Acad Sci USA, 99(6), 3740-3745.
Takai, D., & Jones, P. A. (2003). The CpG island searcher: a new WWW resource. In Silico Biol, 3(3), 235-240.
Tao, Q., Huang, H., Geiman, T. M., Lim, C. Y., Fu, L., Qiu, G. H., et al. (2002). Defective de novo methylation of viral and cellular DNA sequences in ICF syndrome cells. Hum Mol Genet, 11(18), 2091-2102.
US2004248171 Palmisano and Belinsky, filed Mar. 25, 2004, discloses the use of PAX5 as a marker for lung, colon and breast cancers.
US2010028875 Rhytu et al, filed as a PCT application on Aug. 19, 2006, discloses methods for diagnosing cancer and determining prognosis by measuring methylation levels.

SUMMARY

In an embodiment there is disclosed a method for diagnosing or determining the prognosis for gastric cancer in a biological sample from a patient, comprising the step of: detecting in the sample, methylation of a target DNA sequence of at least 15 consecutive base pairs, within a contiguous sequence at least 95% similar to the region consisting of SEQ. ID. NO. 24; and wherein significant methylation level is indicative of poor prognosis for the gastric cancer.

In an embodiment the target sequence may be at least 50 base pairs long and contains a plurality of CpG base pairs.

In an embodiment the method may further comprise comparing the methylation level of the target sequence in the patient sample with the methylation level of non-cancerous cells.

In an embodiment said determining may comprise treating the sample with a reagent that differentially modifies methylated and unmethylated DNA.

In an embodiment the region may consist of SEQ. ID. NO. 11.

In an embodiment the determining may comprise treating the sample with sodium bisulphate.

In an embodiment the determination may be performed by COBRA, BGS, or MSP.

In an embodiment the sample is a blood sample.

In an embodiment the sample is a stool sample.

In an embodiment the determining comprises the steps of: amplifying DNA treated with a restriction enzyme using primers selective for a CpG-containing genomic sequence contained within SEQ ID. NO. 24; and comparing the level of the amplified portion of the genomic sequence in unknown samples to the methylation level in a non-cancerous sample to thereby detect the presence of gastric cancer.

In an embodiment the reagent comprises an enzyme that preferentially cleaves unmethylated DNA.

In an embodiment the amplifying uses the polymerase chain reaction.

In an embodiment the detecting may use a primer or probe selected from the group consisting of: SEQ. IDs. NOS. 1, 2, 5, 6, 7, 8, 9, 10, 15, 16, 17, 18, 19, 20 and 22.

In an embodiment there is disclosed an isolated nucleic acid sequence at least about 95% similar to a region of 10 contiguous base pairs of SEQ. ID. NO. 24.

In an embodiment the isolated sequence is at least 99% similar to a region of about 20 contiguous base pairs of SEQ. ID. NO. 11

In an embodiment there is disclosed a method for detecting gastric cancer in a patient sample, the method comprising detecting in the sample the expression of an RNA sequence at least 95% similar over at least about 15 bases contiguous bases to SEQ. ID. NO. 13, wherein the reduced expression of the sequence is indicative of the presence of gastric cancer. In alternative embodiments the expression may be compared to expression in a control sample.

In an embodiment there is disclosed a method for inhibiting the development of gastric cancer cells, the method comprising the step of: expressing a biologically effective portion of SEQ. ID. No. 23 in the cancer cells to thereby inhibit the growth of the cells.

In an embodiment the expressing comprises demethylating a DNA sequence in the said gastric cancer cells with at least 95% sequence similarity over at least 15 contiguous base pairs to SEQ. ID. NO. 24.

In an embodiment the expressing comprises introducing into said cells an isolated DNA molecule suitable to express a protein at least about 95% similar over about 50 contiguous amino acids to SEQ. ID. NO. 23.

In an alternative embodiment there is disclosed a method for treating gastric cancer in a subject, the method may comprising the step of: treating a patient with a composition suitable to express a biologically effective portion of SEQ. ID. NO. 12, SEQ. ID. NO. 13, or SEQ. ID. NO. 23 in the cancer cells to thereby inhibit the growth of the cells.

In an alternative embodiment there is disclosed a method for treating gastric cancer in a subject, the method comprising the expressing a biologically effective portion of SEQ. ID. NO. 12, SEQ. ID. NO. 13, or SEQ. ID. NO. 23 in the cancer cells to thereby inhibit the growth of the cells.

In alternative embodiments the biologically effective sequences may be introduced directly into the cancer cells.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF EMBODIMENTS

Terms

Figure 1:
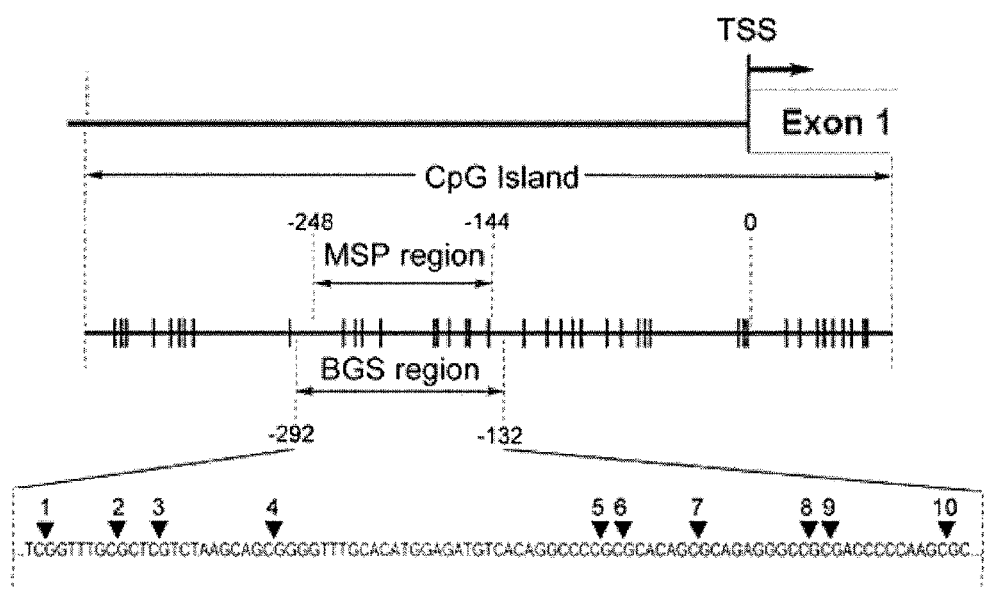
FIG. 1 Shows PAX5 CpG islands in an embodiment. Partial BGS region=SEQ ID NO:25; MSP region, positions –248 to –144=SEQ ID NO:26; BGS region, positions –292 to –132=SEQ ID NO:27.

In this disclosure the following terms have the meanings set forth below:

In this disclosure the term "or" is generally employed in its sense including "and/or" unless the content clearly dictates otherwise.

In this disclosure, the term "biomarker" or "marker" means a substance such as a gene, a measurement of a variable related to a disease that may serve as an indicator or predictor of that disease. Biomarkers or markers are parameters from which the presence or risk of a disease can be inferred, rather than being a measure of the disease itself.

In this disclosure the terms "nucleic acid", "nucleic acid sequence," and the like mean polynucleotides, which may be gDNA, cDNA or RNA and which may be single-stranded or double-stranded. The term also includes peptide nucleic acid (PNA), or any chemically DNA-like or RNA-like material. "cDNA" refers to copy DNA made from mRNA that is naturally occurring in a cell. "gDNA" refers to genomic DNA. Combinations of the same are also possible (i.e., a recombinant nucleic acid that is part gDNA and part cDNA).

In this disclosure the terms "operably associated" and "operably linked," mean functionally coupled nucleic acid sequences.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65.degree. C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are well known in the art and are provided, e.g., in Innis et al. (1990) PCR Protocols, A Guide to Methods and Applications, Academic Press, Inc. N.Y.).

In this disclosure the term "polypeptide" means a polypeptide encoded by a nucleic acid molecule.

In this disclosure the terms "gene expression" and "protein expression" mean and include any information pertaining to the amount of gene transcript or protein present in a sample, as well as information about the rate at which genes, RNA or proteins are being expressed or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

In this disclosure the term "polypeptide" means a molecule comprised of two or more amino acids, preferably more than three. Its exact size will depend upon many factors.

In this disclosure the term "oligonucleotide" means a molecule comprised of two or more nucleotides, preferably more than three. Its exact size will depend upon many factors which, in turn, depend upon the ultimate function and use of the oligonucleotide. In particular embodiments an oligonucleotide may have a length of about 10 nucleotides to 100 nucleotides or any integer therebetween. In embodiments oligonucleotides may be about 10 to 30 nucleotides long, or may be between about 20 and 25 nucleotides long. In embodiments an oligonucleotide may be greater than about 10, 11, 12, 13, 14, 15, 16, 17, 18, 19, 20, 21, 22, 23, 24, or 25 nucleotides long for specificity. In certain embodiments oligonucleotides shorter than these lengths may be suitable.

In this disclosure the term "primer" means an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA or RNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic and prognostic applications, depending on the complexity of the target sequence, the oligonucleotide primer typically contains at least or more than about 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1.1 of the disclosure where their specific applications are indicated.

In this disclosure the term "primer pair", means a pair of primers which hybridize to opposite strands a target DNA molecule or to regions of the target DNA which flank a nucleotide sequence to be amplified.

In this disclosure the term "primer site", means the area of the target DNA or other nucleic acid to which a primer hybridizes.

In this disclosure, the nucleic acids, polynucleotides, proteins, and polypeptides described and claimed refer to all forms of nucleic acid and amino acid sequences, including but not limited to genomic nucleic acids, pre-mRNA, mRNA, polypeptides, polypeptides, polymorphic variants, alleles, mutants, and interspecies homologs that:

(1) have or encode an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein;

(2) specifically bind to or encode polypeptides that specifically bind to antibodies, e.g., polyclonal antibodies, raised against an immunogen comprising a referenced amino acid sequence, immunogenic fragments thereof, and conservatively modified variants thereof;

(3) specifically hybridize under stringent hybridization conditions to a disclosed nucleic acid sequence or to a nucleic acid sequence encoding a disclosed amino acid sequence, and conservatively modified variants thereof, (4) have a nucleic acid sequence that has greater than about 95%, preferably greater than about 96%, 97%, 98%, 99%, or higher nucleotide sequence identity, preferably over a region of at least about 15, 25, 50, 100, 200, 500, 1000, or more nucleotides, to a reference nucleic acid sequence.

A polynucleotide or polypeptide sequence is typically from a mammal including, but not limited to, primate, e.g., human; rodent, e.g., rat, mouse, hamster; cow, pig, horse, sheep, or any mammal. In particular embodiments the polynucleotide and polypeptide sequences disclosed are from humans. The nucleic acids and proteins of the invention include both naturally occurring or recombinant molecules.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

In this disclosure a "cell" may be isolated, may be comprised in a group of cells, may be in culture, or may be comprised in a living subject and may be a mammalian cell and may be a human cell. Similarly "tissue" may comprise any number of cells and may be comprised in a living subject or may be isolated therefrom.

In this disclosure "cancer" means and includes any malignancy, or malignant cell division or malignant tumour, or any condition comprising uncontrolled or inappropriate cell proliferation and includes without limitation any disease characterized by uncontrolled or inappropriate cell proliferation.

In this disclosure the terms "gastric cancer" and "stomach cancer" have the same meaning and mean a cancer of the stomach or of stomach cells. Such cancers may be adenocarcinomas that occur in the lining of the stomach (mucosa) and may be in pylorus, body or cardial (lower, body and upper) parts of the stomach.

In this disclosure the term "gastric cancer cell" means a cell characteristic of gastric cancer, and includes cells which are precancerous.

In this disclosure the term "precancerous" means a cell which is in the early stages of conversion to a cancer cell or which is predisposed for conversion to a cancer cell. Such cells may show one or more phenotypic traits characteristic of the cancerous cell.

In this disclosure the term "purified," or "substantially purified" means nucleic acids or polypeptides separated from their natural environment so that they are at least about 75%, 80, 85, 90 or 95% of total nucleic acid or polypeptide or organic chemicals in a given sample. Protein purity is assessed herein by SDS-PAGE and silver staining. Nucleic acid purity is assessed by agarose gel and EtBr staining.

In this disclosure the term "detection" means any process of observing a marker, or a change in a marker (such as for example the change in the methylation state of the marker, or the level of expression of nucleic acid or protein sequences), in a biological sample, whether or not the marker or the change in the marker is actually detected. In other words, the act of probing a sample for a marker or a change in the marker, is a "detection" even if the marker is determined to be not present or below the level of sensitivity. Detection may be a quantitative, semi-quantitative or non-quantitative observation and may be based on a comparison with one or more control samples. It will be understood that detecting a gastric cancer as disclosed herein includes detecting precancerous cells that are beginning to or will, or have an increased predisposition to develop into gastric cancer cells. Detecting a gastric cancer also includes detecting a likely probability of mortality or a likely prognosis for the condition.

In this disclosure the term "expression vector" means a replicable DNA construct used to express DNA which encodes a desired protein or RNA sequence and which includes a transcriptional unit comprising an assembly of (1) genetic element(s) having a regulatory role in gene expression, for example, promoters, operators, or enhancers, operatively linked to (2) a DNA sequence encoding a desired protein (in this case, an PAX5 protein) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome or in the form of viral sequences which may or may not integrate into the chromosomes. A wide range of expression vectors will be readily recognised and used by those skilled in the art.

In this disclosure the terms "homology", "identity" and "similarity" mean sequence similarity between two peptides or between two nucleic acid molecules. They can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated or "non-homologous" shares less than 40% identity, preferably less than 25% identity with a sequence of the present invention. In comparing two sequences, the absence of residues (amino acids or nucleic acids) or presence of extra residues also decreases the identity and homology/similarity. In particular embodiments two or more sequences or subsequences may be considered substantially or significantly homologous, similar or identical if their sequences are about 60% identical, or are about 65%, 70%, 75%, 80%, 85%, 90%, 91%, 92%, 93%, 94%, 95%, 96%, 97%, 98%, 99%, or higher over a specified region, when compared and aligned for maximum correspondence over a comparison window or designated region, as measured using a BLAST or BLAST 2.0 sequence comparison algorithms with default parameters described below, or by manual alignment and visual inspection such as provided on-line by the National Center for Biotechnology Information (NCBI). This definition also refers to, or may be applied to, the compliment of a test sequence. Thus, to the extent the context allows, for instance where a nucleotide sequence may be expected to naturally occur in a DNA duplex, or may naturally occur in the form of either or both of the complementary strands, then a nucleotide sequence that is complimentary to a specified target sequence or its variants, is itself deemed "similar" to the target sequence and a reference to a "similar" nucleic acid sequence includes both the single strand sequence, its complimentary sequence, the double stranded complex of the strands, sequences able to encode the same or similar polypeptide products, and any permissible variants to any of the foregoing. Circumstances where similarity must be limited to an analysis of the sequence of a single nucleic acid strand may include for example the detection and quantification of the expression of a specific RNA sequence or coding sequence within a cell. The definition also includes sequences that have deletions and/or additions, as well as those that have substitutions. In embodiments identity or similarity may exist over a region that is at least about 10, 11, 12, 13, 14, 15, 16, 17, 18, 19, 10, 21, 22, 23, 24, 25 or more amino acids or nucleotides in length, or over a region that is more than about 10, 15, 20, 25, 30, 35, 40, 45, 50, 55, 60, 65, 70, 75, 80, 85, 90, 95 or more than about 100 amino acids or nucleotides in length.

In this disclosure the term "methylation-sensitive PCR" (i.e., MSP) means a polymerase chain reaction in which amplification of the compound-converted template sequence is performed. Two sets of primers are designed for use in MSP. Each set of primers comprises a forward primer and a reverse primer. One set of primers, called methylation-specific primers, will amplify the compound-converted template sequence if C bases in CpG dinucleotides within the target DNA are methylated. Another set of primers, called unmethylation-specific primers, will amplify the compound-converted template sequences if C bases in CpG dinucleotides within the target DNA are not methylated.

In this disclosure the terms "inhibit" and "suppress" where used with reference to cancer cells or the growth or development thereof, mean and include any effects that result in or comprise slowing or preventing growth or cell division of the cells, killing the cells, disabling the cells, and in any way reducing the viability, rate of division or longevity of the cells and includes any metabolic changes which change the characteristics of the cells in ways more characteristic of benign rather than malignant cell populations.

In this disclosure "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized. Antibodies exist, e.g., as intact immunoglobulins or as a number of well-characterized fragments which can be produced by digestion with various peptidases. The term antibody, as used herein, includes both complete antibodies and also antibody fragments either produced by the modification of whole antibodies, or synthesized de novo using recombinant DNA methodologies (e.g., single chain Fv) or those identified using phage display libraries.

In this disclosure the term "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein.

In this disclosure the term "amplify", means a process whereby multiple copies are made of one particular locus of a nucleic acid, such as genomic DNA or cDNA. Amplification can be accomplished using any one of a number of known means, including but not limited to the polymerase chain reaction (PCR), transcription based amplification and strand displacement amplification (SDA).

In this disclosure the term "polymerase chain reaction" or "PCR", means, a technique in which cycles of denaturation, annealing with primer, and extension with DNA polymerase are used to amplify the number of copies of a target DNA sequence by approximately $10^6$ times or more. The polymerase chain reaction process for amplifying nucleic acid is covered by U.S. Pat. Nos. 4,683,195 and 4,683,202.

In this disclosure the term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In this disclosure a "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

In this disclosure the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Exclusion of Certain Sequences:

It will be understood that in particular embodiments individual examples of sequences, probes, primers, polypeptides or the like may be excluded.

Detection of Nucleic Acids and Polypeptides:

A range of methods for the detection of specific nucleic acid sequences and polypeptides and their application will be readily apparent to those skilled in the art.

Nucleic acid molecules and polypeptides can be detected using a number of different methods. Methods for detecting nucleic acids include, for example, PCR and nucleic acid hybridizations (e.g., Southern blot, Northern blot, or in situ hybridizations). Specifically, oligonucleotides (e.g., oligonucleotide primers) capable of amplifying a target nucleic acid can be used in a PCR reaction. PCR methods generally include the steps of obtaining a sample, isolating nucleic acid (e.g., DNA, RNA, or both) from the sample, and contacting the nucleic acid with one or more oligonucleotide primers that hybridize(s) with specificity to the template nucleic acid under conditions such that amplification of the template nucleic acid occurs. In the presence of a template nucleic acid, an amplification product is produced. Conditions for amplification of a nucleic acid and detection of an amplification product are known to those of skill in the art. A range of modifications to the basic technique of PCR also have been developed, including but not limited to anchor PCR, RACE PCR, RT-PCR, and ligation chain reaction (LCR). A pair of primers in an amplification reaction must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Colo.) to assist in designing primers that have similar melting temperatures. Typically, oligonucleotide primers are 10 to 30 or 40 or 50 nucleotides in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length), but can be longer or shorter if appropriate amplification conditions are used.

In this disclosure the term "standard amplification conditions" refers to the basic components of an amplification reaction mix, and cycling conditions that include multiple cycles of denaturing the template nucleic acid, annealing the oligonucleotide primers to the template nucleic acid, and extension of the primers by the polymerase to produce an amplification product.

Detection of an amplification product or a hybridization complex is usually accomplished using detectable labels. The term "label" with regard to a nucleic acid is intended to encompass direct labeling of a nucleic acid by coupling (i.e., physically linking) a detectable substance to the nucleic acid, as well as indirect labeling of the nucleic acid by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. An example of indirect labeling includes end-labeling a nucleic acid with biotin such that it can be detected with fluorescently labeled streptavidin.

Specific polypeptide sequences may be detected using polyclonal or monoclonal antibodies which can be prepared in conventional ways as will be readily understood and applied by those skilled in the art. Those skilled in the art will readily identify and prepare and raise antibodies to desirable polypeptide sequences to implement the subject matter disclosed and claimed.

The term "probe" with regard to nucleic acid sequences is used in its ordinary sense to mean a selected nucleic acid sequence that will hybridise under specified conditions to a target sequence and may be used to detect the presence of such target sequence. It will be understood by those skilled in the art that in some instances probes may be also be useable as primers, and primers may useable as probes.

Methylation:

In this disclosure, DNA "methylation" refers to the addition of a methyl group to the 5 position of cytosine (C), typically (but not necessarily) in the context of CpG (a cytosine followed by a guanine) dinucleotides. As used herein, "an increased methylation level" or "a significant methylation level" refers to the presence of at least one methylated C nucleotide in a DNA sequence where the corresponding C is not methylated in a normal control sample (such as a DNA sample extracted from a non-cancerous cell or tissue sample, or a DNA sample that has been treated to the methylation on DNA residues), in some embodiments at least 2, 3, 4, 5, 6, 7, 8, 9, 10 or more Cs may be methylated at locations where the Cs are unmethylated in a control DNA sample.

In embodiments, DNA methylation alterations can be detected using a number of different methods. Methods for detecting DNA methylation include, for example, methylation-sensitive restriction endonucleases (MSREs) assay by either southern or polymerase chain reaction (PCR) analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), combined bisulifte restriction analysis (COBRA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or southern blot analysis. In embodiments the degree of methylation of a sequence may be determined using a methylation sensitive DNA cleaving reagent which may be a restriction enzyme and for example may be AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

Articles of Manufacture

This disclosure encompasses articles of manufacture (e.g., kits) that contain one or more nucleic acid molecules, or one or more vectors that encode a nucleic acid molecule. Such nucleic acid molecules are formulated for administration as described herein, and can be packaged appropriately for the intended route of administration. For example, a nucleic acid molecule or a vector encoding a nucleic acid molecule can be contained within or accompanied by a pharmaceutically acceptable carrier.

Kits of according to embodiments can include additional reagents (e.g., buffers, co-factors, or enzymes). Pharmaceutical compositions according to embodiments can include instructions for administering the composition to an individual. Kits may also contain a control sample or a series of control samples that can be assayed and compared to the biological sample. Each component of a kit may be enclosed within an individual container and all of the various containers are within a single package.

Compositions and Delivery of Compositions to Target Cells

In certain embodiments there are disclosed compositions for delivery to target cells. It will be understood that the compositions used in particular embodiments may be used in combination with suitable pharmaceutically acceptable carriers or excipients and may be used in any suitable dosage forms. Those skilled in the art will readily identify, select from, and use the foregoing to suit the circumstances in question. Where a cell to be treated is comprised in the body of a subject the methods disclosed may be implemented and the compositions disclosed may be delivered to the cell in any conventional ways including without limitation the delivery of the tetrose or prodrug, orally, parentally, enterally, intramuscularly, subcutaneously, intravenously, or by inhalation and may be delivered in combination with suitable carriers or excipients, in suitable dosage forms including without limitation tablets, capsules, subdermal pumps or other routes useful to achieve an effect. Alternative delivery methods may include osmotic pumps, implantable infusion systems, intravenous drug delivery systems, and refillable implantable drug delivery systems. Delivery by inhalation may comprise delivery using nebulizers, metered dose inhalers, powder inhalers, all of which are familiar to those skilled in the art. Suitable methods, compositions and routes of delivery will be readily recognised and implemented by those skilled in the art.

Selected Embodiments

In a first series of embodiments there is disclosed a method for diagnosing or providing a prognosis for a gastric cancer in a biological sample. The method may comprise the step of detecting in the sample, methylation of a target DNA sequence of at least about 15 consecutive base pairs, within a contiguous sequence at least 95% similar to the region consisting of SEQ. ID. NO. 24. It will be understood that in embodiments the target DNA sequence may be at least about 10 base pairs long or may be at least about 15, 20, 25, 30, 35, 40, 45, 50 or more base pairs long and the degree of sequence similarity may be at least about 90%, 91%, 92%, 93%, 94%, 95%, 96%, 97%, 98%, 99%, or 100%. In alternative embodiments the target DNA sequence may be within a contiguous sequence at least 95% similar to the region consisting of SEQ. ID. NO. 11.

In an embodiment significant methylation level may be indicative of poor prognosis for the gastric cancer. In alternative embodiments the target sequence may be at least about 50 base pairs long and may contain a plurality of CpG base pairs. In particular alternative embodiments the target sequence may comprise about 1, 2, 3, 4, 5, 6, 7, 8, 9, 10 or more CpG base pairs and the significant methylation may relate to any one or more of such CpG base pairs either alone or in combination with any other one or more of such CpG base pairs.

In alternative embodiments the method may further comprise comparing the methylation level of the target sequence in the patient sample with the methylation level of non-cancerous cells or of other suitable control samples, all of which will be readily apparent to those skilled in the art. In alternative embodiments the determining may comprise treating the sample with a reagent that differentially modifies methylated and unmethylated DNA. In alternative embodiments the reagent may comprise a restriction enzyme that preferentially cleaves unmethylated DNA or preferentially cleaves methylated DNA. In further alternative embodiments the determining may comprise treating the sample with sodium bisulphate or may be performed by combined bisulfite restriction analysis (COBRA). In embodiments the sample may be a blood sample or a stool sample.

In alternative embodiments the determining may comprise the steps of: a) amplifying DNA treated with a restriction enzyme using primers selective for a CpG-containing genomic sequence contained within SEQ ID. NO. 24 or SEQ. ID. NO. 11; and b) comparing the level of the amplified portion of the genomic sequence in unknown samples to the methylation level in a non-cancerous sample to thereby detect or assess the prognosis of the gastric cancer. In alternative embodiments the amplifying may use the polymerase chain reaction. In alternative embodiments the detecting may use a primer or probe selected from the group consisting of: SEQ. IDs. NOS. 1, 2, 5, 6, 7, 8, 9, 10, 15, 16, 17, 18, 19, 20, 21 or 22.

In a second series of embodiments there is disclosed an isolated nucleic acid sequence that may be at least about 10 base pairs long and 95% identical to a fragment of SEQ. ID. NO. 24 or SEQ ID. NO. 11. In alternative embodiments the isolated sequence may be at least about 11, 12, 13, 14, 15, 16, 17, 18, 19, 20, 21, 22, 23, 24, 25, 30, 35, 40, 45, 50 or more base pairs long and may be at about 90%, 91%, 92%, 93%, 94%, 95%, 96%, 97%, 98%, 99%, or 100% similar to the corresponding fragment. In an alternative embodiments there is disclosed a kit for detecting gastric cancer, and the kit may comprise an isolated nucleic acid sequence according to any of the other embodiments. The kit may further comprise instructions and further reagents.

In a third series of embodiments there is disclosed a method for detecting gastric cancer in a patient sample, the method comprising detecting in the sample the expression of an RNA sequence at least 95% similar over at least about 15 bases to SEQ. ID. NOs. 12, or 13 or a protein sequence at least about 95% similar over at least about 15 amino acids to SEQ. ID. No. 23 and wherein the reduced expression of the sequence when compared to a non cancerous sample is indicative of the presence of gastric cancer. In embodiments the non-cancerous sample may comprise RNA or protein sample extracted from a non-cancerous cell or tissue sample, from normal gastric mucosa. In alternative embodiments the sequence similarity may extend over about 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 400, 600, 800 or more base pairs or encoded amino acids and may be about 90%, 91%, 92%, 93%, 94%, 95%, 96%, 97%, 98%, 99%, or 100%. In embodiments the level of the sequence expressed may be compared to the level of the sequence expressed in a non-cancerous control. In embodiments the detecting may be achieved using primers shown as SEQ. ID. NOs. 1, 2, 3 and 4.

In a third series of embodiments there is disclosed a method for inhibiting the development of gastric cancer cells. The method may comprise the step of expressing in the cancer cells a biologically effective portion of SEQ. ID. No. 12, SEQ. ID. NO. 13, or SEQ. ID. NO. 23 to thereby inhibit the growth of the cells. In embodiments the sequence identity may extend over about 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 400, 600, 800 or more base pairs and may be about 90%, 91%, 92%, 93%, 94%, 95%, 96%, 97%, 98%, 99%, or 100%. In alternative embodiments the expressing may comprise introducing into the cells an isolated DNA molecule comprising a PAX5 coding sequence operatively linked to a promoter. The promoter may be suitable to drive the constitutive or exogenously triggerable expression of the PAX 5 coding sequence. In embodiments the PAX 5 coding sequence may be at least about 90%, 91%, 92%, 93%, 94%, 95%, 96%, 97%, 98%, 99%, or 100% similar to a region comprising at least 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 400, 600, 800 or more nucleotides of SEQ. ID. NO. 12 or SEQ. ID. NO. 13 or SEQ. ID. NO. 23 and in an embodiment the similarity may extend throughout SEQ. ID. NO. 12 or SEQ. ID. NO. 13 or SEQ. ID. NO. 23.

In embodiments the expressing may comprise demethylating a DNA sequence in the gastric cancer cells with at least 95% sequence similarity over at least 15 contiguous base pairs to SEQ. ID. NO. 24 or SEQ. ID. NO. 11. In embodiments the expressing may comprise introducing into the cells an isolated DNA molecule comprising a PAX-5 coding sequence operatively linked to a promoter.

In an alternative embodiment there is disclosed a method for treating gastric cancer in a subject, and the method may comprise the step of: expressing a biologically effective portion of SEQ. ID. 12 or a biologically effective portion of SEQ. ID. NO. 13. or a biologically effective portion of SEQ. ID. NO. 24, or a biologically effective sequence at least about 90%, 91%, 92%, 93%, 94%, 95%, 96%, 97%, 98%, 99%, or 100% similar to a region comprising at least 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 400, 600, 800 or more nucleotides of any of the foregoing in the cancer cells to thereby inhibit the growth of the cells. It is predicted that the expression may be achieved by treating the subject with a suitable dosage form of a demethylating agent, or by administering to the patient by injection, or other suitable methods, the biologically effective portion of the sequence in a suitable vector or under the control of a suitable promoter. In embodiments the method for treating comprises treating or administering to a patient a composition suitable to express the biologically effective sequences. The compositions may comprise suitable vectors and constructs are disclosed in the Examples section hereof and methods of administering, adapting, varying and making such constructs and inducing the expression of the desired sequences in a target cell will be readily apparent to those skilled in the art. Similarly the biologically effective portions of the sequences may be introduced directly into the desired cells.

Further Alternative Embodiments

In embodiments, the materials and methods disclosed may be applied to assess the presence or progress of a cancer, its prognosis, or other factors relating to the cancer. All of which will be readily understood by those skilled in the art.

EXAMPLES

The following are examples that illustrate materials, methods, and procedures for practicing the subject matter of the embodiments disclosed. It should be understood that the examples and embodiments described herein are for illustrative purposes only and that various modifications or changes in light thereof will be suggested to persons skilled in the art and are to be included within the spirit and purview of this application.

1. Materials and Methods 1.1 Human Gastric Specimens 1.1.1 Tissue Samples

There are three cohorts of human samples involved in this study: 1) Normal gastric mucosa biopsies for methylation status profiling were from the Endoscopy Center of Prince of Wales Hospital. 2) Gastric Cancer ("GC") tissues and their corresponding adjacent non-cancerous tissues, which were at least 5 cm away from the tumor edge, were obtained from GC patients during endoscopy. These samples were used in the PAX5 gene expression level comparison. 3) Paraffin embedded GC samples also for checking methylation status were from Guangzhou Zhong Shan Hospital, China. The GC samples were staged according to the American Joint Committee on Cancer TNM System. All fresh tissues were snap frozen in liquid nitrogen and then stored at −80° C. until further processing.

To evaluate the methylation status and the clinical significance of PAX5 in GC patients, 161 GC specimens and 19 normal gastric biopsies were used for the assay of BGS. GC group included 107 male and 54 female, with average age 56.8±12.6, and normal group included 7 male and 12 female, with average age 51.9±17.2. Other clinicopathologic features such as Helicobacter pylori (H. pylori) infection, TNM stages and differentiation status were also determined. By using rapid urease test (RUT), 29 patients were found infected by H. pylori, and 70 patients were H. pylori infection negative. The patient number in TNM stage I, II, III and IV were 20, 23, 49 and 52, respectively. There were 94 patients with low differentiation GC, and 43 patients had developed moderate or high differentiation GC. The patients' information was provided by the Guangzhou Zhong Shan Hospital. Some of the information was not complete. Informed consent was given to all the patients and controls, and the study protocol was approved by the Clinical Research Ethics Committee of the Chinese University of Hong Kong.

1.1.2 Tumor Cell Line

Sixteen tumor cell lines from gastrointestinal tract were used, including 8 GC cell line (AGS, BGC823, Kato III, MKN28, MKN45, N87, SNU1 and SNU16) and 8 Colorectal cancer (CRC) cell line (Caco2, DLD1, HCT116, HT29, LoVo, LS180, SW480 and SW620) were purchased from the ATCC (American Type Culture Collection, Manassas, Va., USA). All the GC cell lines and 3 CRC cell line (LoVo, LS180 and SW480) were cultured in RPMI 1640 medium (Sigma-Aldrich, St Louis, Mo., USA) supplemented with 10% fetal bovine serum (FBS) (Sigma-Aldrich). The Dulbecco's Modified Eagle's Medium (DMEM) (Sigma-Aldrich) with 10% FBS was used to culture HT29, SW620 and Caco2. The cultivation of cell line HCT116 was performed by using McCoy's 5a medium (Sigma-Aldrich) with 10% FBS. All these cell lines were incubated in an incubator with 95% air and 5% $CO_2$ at 37° C. Culture media were renewed every two to four days. Cells were split at 1:3~1:4 ratio using 0.25% Trypsin-EDTA solution (Invitrogen, Carlsbad, Calif., USA).

1.2 Bioinformatics Analysis of PAX5 Gene

The online database of University of California Santa Cruz Genome Bioinformatics (UCSC) website genome.ucsc.edu, was used to obtain the related information about PAX5 gene.

CpG islands in the PAX5 gene promoter region were predicted by CpG Island Searcher (http://cpgislands.usc.edu/)

(Takai & Jones, 2003) Takai, D., & Jones, P. A. (2003). The CpG island searcher: a new WWW resource. In Silico Biol, 3(3), 235-240. CpG islands are defined as DNA region greater than 500 bp with GC content above 55% and an observed/expected CpG ratio above 0.65 (Takai & Jones, 2002) Takai, D., & Jones, P. A. (2002). Comprehensive analysis of CpG islands in human chromosomes 21 and 22. Proc Natl Acad Sci USA, 99(6), 3740-3745. The foregoing methods and tools will be readily apparent to those skilled in the art.

1.3 Gene Expression Analysis

1.3.1 RNA Isolation

Total RNA was isolated using Quizol reagent (Qiagen; Valencia, Calif., USA). First, about $5-10 \times 10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000 (NanoDrop Technologies, Wilmington, Del., USA). The purified RNA was store at −80° C. until using.

1.3.2 cDNA Synthesis

MultiScribe Reverse Transcriptase Kit (Applied Biosystems, Foster City, Calif., USA) was used to synthesize cDNA. The reaction mixture contained 1× Reverse Transcriptase buffer, 1×dNTP, 1× random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. 5 min to inactivate the enzymes. The cDNA was stored at −80° C. until other application.

1.3.3 Semiquantitative Reverse Transcription PCR (RT-PCR)

Semiquantitative RT-PCR was performed in a total volume of 25 μL reaction containing GeneAmp 1×PCR Buffer II (Applied Biosystems), 2.5 mM $MgCl_2$, 200 μM each of dNTP, 200 nM each of primers, 0.5 U of AmpliTaq Gold DNA polymerase (Applied Biosystems) and 30~50 ng cDNA. The PCR program started with an initial denaturation at 95° C. for 10 min, followed by 32-35 cycles (94° C. for 30 sec, 58° C. for 30 sec, and 72° C. for 30 sec) of amplification, with a final extension at 72° C. for 10 min. The PCR bands were visualized under ultraviolet light and photographed. The expression of the target gene was normalized by the expression of house keeping gene β-actin, which served as an internal control. All primers used to amplify the transcripts are listed in Table 1.1.

1.3.4 Real-Time Quantitative PCR (qPCR)

For the real-time quantitative RT-PCR, the PAX5 expression was determined using the ABI PRISM 7500 Sequence Detection System (Applied Biosystems). The qPCR was performed according to the protocol of the SyberGreen Master Mix (Applied Biosystems) in a total volume of 25 μL reaction containing 1×SyberGreen Master Mix, 100 nmol/L primers and 30 ng cDNA template. The qPCR condition was 95° C. for 10 min, then 40 cycles of 95° C. for 15 sec, 58~60° C. (according to the annealing temperature of the primers) for 40 sec, 72° C. for 30 sec. The gene expression data was analyzed using the relative quantification $2^{-\Delta\Delta C_T}$ method (Livak & Schmittgen, 2001) Livak, K. J., & Schmittgen, T. D. (2001). Analysis of relative gene expression data using real-time quantitative PCR and the 2(-Delta Delta C(T)) Method. Methods, 25(4), 402-408, and will be well known to those skilled in the art.

1.3.5 mRNA Expression Array

Gene expression profiles in GC cell line with or without PAX5 protein were analyzed by the Cancer Pathway Finder PCR Array systems (SABiosciences, Frederick, Md., USA). This array system can detect 84 genes representative of the six biological pathways involved in transformation and tumorigenesis (http://www.sabiosciences.com). Real-time PCR using ABI PRISM 7500 Sequence Detection System (Applied Biosystems) was performed according the protocol. Simply mix the cDNA template with the appropriate ready-to-use PCR master mix (supplied by kit), aliquot 25 μL to each well of the 96-well plate, and then run the real-time PCR cycling program: 1) 95° C. for 10 min, 2) 40 cycles of 95° C. for 15 sec and 60° C. for 1 min. The expression results were analyzed by web based PCR Array Data Analysis Software according to the instruction (http://www.sabiosciences.com/perarraydataanalysis.php). Gene expression up-regulation or down-regulation with fold-changes of 1.5 times was considered to be of biological significance.

1.3.6 Protein Extraction

Protein was prepared by using CytoBuster Protein Extraction Reagent (Merck Chemicals, Nottingham, UK). The cells were pelleted at 3000 g for 10 min. Then the pellet was resuspended in CytoBuster using 100 μL per $10^6$ cells. The mixture was incubated at room temperature for 5 min. Then centrifuge the tube for 10 min at 4° C. at 15,000 g and transfer the supernatant to a fresh tube.

1.3.7 Sodium Dodecyl Sulfate-Polyacrylamide Gel Electrophoresis (SDS-PAGE) and Western Blot Forty micrograms of protein were separated by 5% upper gel and 10% lower gel. After SDS-PAGE, the protein was transfer to an equilibrated polyvinylidene difluoride (PVDF) membrane (Amersham Biosciences, Buckinghamshire, UK) by semi-dry machine at 15 V for 40 min. The membrane was blocked in 5% non-fat milk dissolved by TBS/T solution (Tris-buffered saline (Invitrogen) and 0.1% Tween 20 (Sigma-Aldrich)) at room temperature for 1 hr with shaking. After blocking, the membrane was incubated in primary antibody diluted in 5% non-fat milk at 4° C. overnight with shaking. After incubation with the secondary antibody at room temperature for 1 hr, the proteins were detected by enhanced chemiluminescence (ECL, Amersham Corporation, Arlington. Heights, Ill., USA).

1.4 DNA Methylation Analysis

1.4.1 Genomic DNA Extraction

Genomic DNA from GC cell lines and tissue samples were isolated by using DNA mini kit (Qiagen) according to the kit protocol. About 25 mg samples were lysed in 180 μL of QIAamp ATL buffer and 20 μL of proteinase K in a 1.5 mL microcentrifuge tubes for 1 hour at 56° C. Four microliter of RNase A (100 mg/ml, QIAgen) was added and mixed by pulse-vortexing for 15 s followed by 2 min incubation at room temperature. Then 200 μL of AL buffer was added to the lysate and samples were incubated for 10 min at 70° C. After adding 200 μL of absolute ethanol, the solution was mixed by pulse-vortexing for 15 s. Then lysates were purified over a QIAamp column as specified by the manufacturer. The genomic DNA was diluted in 200 μL DNase-free $H_2O$. The quality and quantity of DNA were determined by measuring absorbance at 260 nm/280 nm using NanoDrop ND-1000 (NanoDrop).

1.4.2 Sodium Bisulfite Conversion

The genomic DNA was modified by sodium metabisulfite as description by Tao et al. (2002). Briefly, 5 μg genomic DNA in 30 μL TE buffer (Sigma-Aldrich) was mixed with 3.3 μL of 3 mM NaOH to a final concentration of 0.3 mM and incubate at 37° C. for 15 min. Denatured DNA was mixed with 333 μL of bisulfite solution and treated in darkness for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the protocol supplied by the kit. DNA was then treated with 0.3 M NaOH at 37° C. for 15 min and precipitated with 3 M ammonium acetate and 3 volumes of ethanol. Recovered DNA was dissolved in 100 μL TE buffer (pH 8.0) and stored at −20° C.

1.4.3 Demethylation Treatment using 5-aza-2'-deoxycytidine ("5-Aza")

Cells were seeded at a density of $1\times10^5$/100-mm dishes and grew for 24 hr. Cells were then treated with 2 μM 5-aza-2'-deoxycytidine ("5-Aza") (Sigma-Aldrich) for 5 days. The 5-Aza was replenished every day. The gene expression of PAX5 was evaluated using semiquantitative RT-PCR.

1.4.4 Methylation Specific PCR (MSP)

Methylation specific and unmethylation specific primers were designed to assess methylation status in the GC and CRC cell lines. The mixture for PCR contained 1×PCR Buffer II (Applied Biosystems), 2 mM $MgCl_2$, 200 μM each of dNTP, 600 nM each of primers, 0.5 U of AmpliTaq Gold DNA polymerase (Applied Biosystems) and 20 ng bisulfite treated DNA. The PCR program was 95° C. for 10 min, followed by 38 cycles (94° C. for 30 sec, 60° C. for 30 sec, and 72° C. for 30 sec) of amplification, with a final extension at 72° C. for 5 min. Bands of MSP were observed under ultraviolet light and photographed.

1.4.5 Bisulfite Genomic Sequencing (BGS)

Direct BGS with PCR product was used to profile methylation status in normal and GC samples. Sequencing was performed using the BigDye Terminator Cycle Sequencing kit version 1.0 (Applied Biosystems). Briefly, 10-μL mixture, including 2 μL of BigDye-Terminator Ready Reaction Mix, 3.2 pmol specific primers and 10 ng of PCR product were added for sequencing reaction as follows: 25 cycles of 96° C., 30 sec, 50° C., 15 sec; 60° C., 4 min. A 60-μL mixture of 10 μL of sodium acetate (5 M, pH 5.2) and 50 μL of absolute ethanol were added into each reaction product: After storage at −80° C. for 20 min, the mixture was centrifuged at 3,700 rpm for 30 min at 4° C. The supernatant was discarded and the pellets were washed once with 100 μL of 75% ethanol. Finally, the dried pellets were dissolved in 10 μL of Hi-Di Formamide (Applied Biosystems). After denaturation at 95° C. for 5 min, the sequencing solution was kept on ice for 2 min and then analyzed by the ABI 3100 Genetic analyzer (Applied Biosystems). Sequences were analyzed by using SeqScape software (Applied Biosystems). Methylation percentage of each CpG site was calculated according this formula: Methylation %=$H_C/(H_C+H_T)\times100\%$, ($H_C$=Height of peak C, $H_T$=Height of peak T).

1.5 Biological Function Analysis

1.5.1 Cloning of PAX5 and Construction of Expression Vector

The full-length cDNA of PAX5 gene expression vector was generated by PCR-cloning. Total RNA from human stomach (Ambion, Austin, Tex., USA) was reverse transcribed into cDNA. Sequence corresponding to the open reading frame (ORF) of PAX5 was amplified by PCR. PCR product was subcloned into the pcDNA3.1 TOPO TA expression vector according to the manufacturer's guideline (Invitrogen). Briefly, 1 μL PCR product was ligated into the 0.5 μL TOPO vector in a total volume of 2.5 μL containing 240 mM NaCl and 12 mM $MgCl_2$. The mixed reaction was incubated for 30 min at room temperature before heat shock transformation.

The heat-shock transformation was performed using JM109 chemically competent *Escherichia coli* (*E. coli*) cell (Promega, Madison, Wis., USA). The JM109 competent cells (50 μL) were thawed on ice, and 2 μL of ligation product was added into the cells. After incubation on ice for 20 min, the cells were heated shock for 45 sec at 42° C. without shaking in a water bath and then immediately transferred the tube on ice for 5 min. S.O.C. medium (250 μL) was added to the cells and the tube was shaken at 220 rpm at 37° C. for 1 hr in a shaking incubator. After incubation, 150 μL cells were spread on Luria-Bertani (LB) agar plates containing 0.1 mg/ml ampicillin and incubated overnight at 37° C.

Bacterial colonies were identified by PCR. Positive colonies were cultured in LB medium with 0.1 mg/ml ampicillin. Insert DNA was checked by sequencing. Plasmids with non-mutation target gene were isolated using HiSpeed Plasmid Maxi Kit (Qiagen). Briefly, bacterial were cultured in 1 mL LB medium containing 0.1 mg/ml ampicillin at 37° C. overnight with shaking at 250 rpm. Then, 0.5 mL bacterial culture was further inoculated into 100 mL LB medium containing 0.1 mg/ml ampicillin and grew at 37° C. for 16 hr with shaking at 250 rpm. Bacterial pellet was harvested by centrifugation at 6000 g for 15 min at 4° C. The pellet was resuspended in 10 mL Buffer P1. Bacterial protein, chromosomal and plasmid DNA were denatured with 10 mL Buffer P2. The tube was inverted upside down for six times and then placed at room temperature for 5 min. The mixture was neutralized with 10 mL Buffer P3, followed by incubation at room temperature for 10 min. Debris within the cell lysate was cleared by filtrating with the QIAfilter cartridge. The filtrated lysate was applied to the resin column supplied in the kit through gravity flow, and plasmid DNA was bound to the resin column. The column was washed with 30 mL QC buffer by gravity flow to remove all contaminants during plasmid preparations and carbohydrates from bacterial strains. Plasmid DNA was eluted with 15 mL Buffer QF. DNA was precipitated by isopropanol precipitation and the DNA pellet was washed with 70% ethanol. The DNA pellet was air-dried and dissolved with 1 mL DNase-free $H_2O$.

1.5.2 PAX5 Gene Transfection

Cells were seeded at $1\times10^4\sim2.5\times10^4$ cells on a 24-well plate without antibiotics for about 24 hr till the cell density reached about 90% confluent. Cells were then transfected with 0.8 μg PAX5 and control vector (pcDNA3.1) respectively using Lipofectamine 2000 (Invitrogen). Lipofectamine 2000 (2.0 μL) diluted in 50 μL Opti-MEM (Invitrogen) was incubate at room temperature for 5 min. Then, plasmid DNA diluted in 50 μL Opti-MEM was combined with the Lipofectamine mixture. After 24~48 hr incubation at 37° C. in a 5% $CO_2$ incubator, cells were harvested for testing of transgenic expression. For stable cell lines, cells were passaged at a 1:10 ratio into fresh growth medium with proper concentration of neomycin (G418) (Invitrogen). Stable transfection cells were harvested after 14-21 days of selection for functional assays.

1.5.3 Colony Formation Assay

Two days after transfection, cells were subsequently split at 1:20 ratio on six-well plates with RPMI1640 in 10% FBS containing 500 μg/mL neomycin (G418). After 14-18 days of selection, cells were fixed with 70% ethanol for 10 min and stained with 0.5% crystal violet solution for 10 min. Colony with more than 50 cells per colony was counted. The experiment was conducted in three independent triplicates.

1.5.4 Cell Viability Assay

MTS assay, which is the short form of 3-(4,5-dimethylthiazol-2-yl)-5-(3-carboxymethoxyphenyl)-2-(4-sulfophenyl)-2H-tetrazolium assay, was performed using CellTiter 96 AQ$_{ueous}$ One Solution Cell Proliferation Assay kit (Promega). Transfected cells were trypsinized and counted. Cells were diluted to 5,000 cells per 100 µL in RPMI1640 medium. For each well in the 96-well plate, 100 µL of cells were seeded. The plate was incubated at 37° C. in a 5% $CO_2$ incubator. After 48 hr, 20 µL MTS reagent was added into the culture medium. The culture was incubated at 37° C. in a $CO_2$ incubator for 30 min to 2 hr. Absorbance of the samples was measured at 490 nm 48 hr post transfection. This experiment was replicated three times.

1.5.5 Wound Healing Assay

The wound healing assay allows the study of cell migration. Briefly, trypsinized cells with a concentration of $5\times10^5$ cells per well were seeded in a 6-well plate in complete medium. The cells were incubated at 37° C. in a 5% $CO_2$ incubator for 24 hr. After removing the culture medium from cells, 3 scratch wounds across each well were made by using a very fine pipette tip. The loosely held cells were removed by washing with 1× Phosphate buffered saline (PBS) twice. The starvation medium with half concentration FBS was added in each well. Images of the wounds were taken at 0 hr, 24 hr and 48 hr. This assay was replicated twice.

1.5.6 Invasion Assay

Matrigel invasion assay was performed using the 24-well matrigel biocoated invasion chamber (BD Biosciences, Bedford, Mass., USA) according to the protocol of the kit. Stable cells with PAX5 gene or control vector pcDNA3.1 were used in this assay. For each matrigel transwell, 0.5 mL of cell suspension with $2.5\times10^4$ cells was added. As chemoattractant, 0.75 mL of culture medium containing 10% FBS and 0.1% bovine serum albumin (BSA) was added in the lower chamber. The chambers were incubated for 24 hr in an incubator at 37° C. with 5% $CO_2$ atmosphere. Non-invading cells were removed from the upper surface of the membrane. Cells that invaded through the matrigel membrane were stained using 0.5% crystal violet solution. The number of invaded cells was count under a microscopy. Data were collected and analyzed from three independent assays.

1.5.7 Cell Cycle Analysis and Annexin V Apoptosis Assay

Propidium iodide (PI) is an intercalating agent and a fluorescent molecule that can be used to stain DNA. This dye is excluded by viable cells but can penetrate cell membranes of dying or dead cells. Cells staining with PI are usually analyzed by flow cytometry to evaluate cell viability or DNA content in cell cycle analysis. For cell cycle analysis, the cells were harvested and washed twice by 1×PBS buffer. Cold 70% ethanol was used to fix the cell at 4° C. overnight. The fixed cell was wash twice by 1×PBS. PI staining solution (50 µg/mL PI and 100 µg/mL RNase A in 1×PBS buffer) was added to the cells and mixed well. The mixture was placed at 4° C. for 30 min until analyzed by flow cytometry. About 20,000 cells were counted, and the results were analyzed by ModFit 3.0 software (Verity Software House, Topsham, Me., USA).

Annexin V is a protein which could bind the cell membrane after apoptosis have occurred and before membrane integrity has been lost. The proportion of apoptotic cells was evaluated using Annexin V and PI double staining. Briefly, the cells washed with 1×PBS was resuspended in 100 µL ice-cold annexin-binding buffer (10 mM HEPES, 140 mM NaCl and 2.5 mM CaCl2, pH 7.4) containing 5 µL Annexin V conjugated with Alexa Fluor 488 (Invitrogen) and 2 µL PI staining (50 µg/mL) (BD Pharmingen, San Jose, Calif., USA). After incubation for 15 min at room temperature, cells were mixed with additional 400 µL of ice-cold annexin-binding buffer and analyzed using flow cytometry.

1.5.8 In Vivo Tumorigenicity

BGC823 cells ($1\times10^6$ cells in 0.1 mL PBS) transfected with pcDNA3.1-PAX5 or pcDNA3.1 only were injected subcutaneously into the dorsal left flank of 5-week-old male Balb/c nude mice, separately. After tumors were visible, the tumor size was measured every 2 days until 3 weeks. Tumor volume ($mm^3$) was estimated by measuring the longest and shortest diameter of the tumor and calculating as follows: volume= (shortest diameter)$^2$×(longest diameter)×0.5. Care of animals and all experimental procedures were approved by the Animal Ethics Committee of the Chinese University of Hong Kong. After 3 weeks, the mice were sacrificed, and the tumors were weighed and fixed in formalin for histological analysis.

1.6 Histologic Assay

1.6.1 Preparation of Paraffin Tissue Sections

After the mice were sacrificed, the tumors were removed and fixed by formalin. Then the fixed tissues were embedded in paraffin wax. Paraffin blocks were cut into 4-6 micron thick, and floated on a water bath containing distilled water. The sections were picked up on slides. The slides were dried in drying oven or at room temperature overnight.

1.6.2 Immunostaining

Immunohistochemical staining was performed with Histostain-Plus Kits (Invitrogen). Briefly, paraffin sections were deparaffinized with xylene and rehydrated in a graded series of ethanol. Slides were submerged in Peroxidase Quenching Solution (3% hydrogen peroxide) for 10 min. Then the slides were handled with microwave epitope retrieval for 10 min, and washed 3 times with PBS for 2 min. Serum blocking solution was added in, and incubated for 10 min. It should not be rinsed at this step. Then the primary antibody was applied overnight at 4° C. After that, the slides were rinsed 3 times with PBS for 2 min. The slides were incubated with enough biotinylated secondary antibody for 30 min, and were rinsed 3 times with PBS for 2 min. After rinsing, enzyme conjugate was applied in a humidified chamber for 30 min, followed with rinsing 3 times by PBS for 2 min. The color was developed in a diaminobenzidine (DAB) substrate solution. Finally, the sections were counterstained with hematoxylin and mounted with histomount.

1.6.3 In Situ DNA Nick End Labeling

Terminal deoxynucleotidyl transferase-mediated dUTP-digoxigenin nick end labeling (TUNEL) assay was performed with Dead End™ Colorimetric TUNEL System (Promega). Briefly, paraffin sections were dewaxed, rehydrated, rinsed with distilled water and washed in 1×PBS. Then the tissues were digested with 20 µg/mL proteinase K at room temperature for 25 min. Refixation of tissues were done with 10% buffered formalin in PBS. Following the application of an equilibration buffer, the sections were incubated in working strength TdT enzymes that contained Biotinylated Nucleotide Mix at 37° C. for 60 min. The reaction was stopped by the application of working strength stop/wash buffer. After washing, quenching of endogenous peroxidase was performed with 0.3% hydrogen peroxide for 5 min. Streptavidin HRP solution was applied in a humidified chamber for 30 min at room temperature. The color was developed in a DAB substrate solution. Sections were then counterstained with haematoxylin. Cell nuclei with brown signal were regarded as programmed death cells. The apoptosis cell ratio was calculated as percentage of positive cell in at least 1,000 cells.

1.7 Statistical Analysis

The difference of PAX5 mRNA expression level between tumor and adjacent non-tumor primary gastric tissues was analyzed by paired t-test. Independent samples t-test was performed to analyze statistical significant difference between control and PAX5 over-expressed cells in colony formation, MTS assay, cell cycle, annexin V-PI double staining assay, TUNEL, invasion assay and tumor weight in nude mice. The chi-square test was employed for analysis of patient features. Receiver Operating Characteristic (ROC) curve was utilized to estimate the cut off value of the methylation percentage for determination of methylation status. Kaplan-Meier survival curve and log-rank test were used to evaluate overall survival data corresponding to PAX5 methylation status. The difference in tumor growth rate between the 2 groups of mice stably transfected with PAX5 expression vector and control vector was determined by repeated measures analysis of variance (ANOVA). Data were considered statistically significant when P is less than 0.05; and very significant when P is less than 0.01.

TABLE 1.1

DNA sequences of primers used in this study.

| Primer name | Sequence (5'-3') | |
|---|---|---|
| A) RT-PCR primers for detecting PAX5 mRNA expression | | |
| PAX5RTF | GTCCATTCCATCAAGTCCTG | SEQ. ID. NO. 1 |
| PAX5RTR | TTGCTGACACAACCATGGCT | SEQ. ID. NO. 2 |
| B) Cloning primers for cloning PAX5 protein coding sequence | | |
| PAX5CloneF | ATATaagcttGTCCATTCCATCAAGTCCTG | SEQ. ID. NO. 3 |
| PAX5CloneR | ATATctcgagAGGGTCAGTGACGGTCATA | SEQ. ID. NO. 4 |
| C) BGS primers used for for bisulfite genomic sequencing of a CpG island of PAX5 | | |
| PAX5BGSF | gTTTTTTTAAAAGTATTTGTTTGGT | SEQ. ID. NO. 5 |
| PAX5BGSR | gCACCTTCTATTAAAACATAC | SEQ. ID. NO. 6 |

| MSP primer | Sequence (5'-3') | Sequence region amplified | |
|---|---|---|---|
| D) | | | |
| PAX5mF1 | TGAATCGGAGTAAATCGGAAC | -352 to -212 | SEQ. ID. NO. 15 |
| PAX5mR1 | CCCGCTACTTAAACGAACG | | SEQ. ID. NO. 16 |
| PAX5uF1 | GGTGAATTGGAGTAAATTGGAAT | | SEQ. ID. NO. 17 |
| PAX5uR1 | CCCCACTACTTAAACAAACA | | SEQ. ID. NO. 18 |
| E) | | | |
| PAX5mF2 | AAATAAAAATTCGGTTTGCGTTC | -248 to -144 | SEQ. ID. NO. 7 |
| PAX5mR2 | AAACATACGCTTAAAAATCGCG | | SEQ. ID. NO. 8 |
| PAX5uF2 | TAAAAATAAAAATTTGGTTTGTGTTT | | SEQ. ID. NO. 9 |
| PAX5uR2 | TTAAAACATACACTTAAAAATCACA | | SEQ. ID. NO. 10 |
| F) | | | |
| PAX5mF3 | GCGTATGTTTTAATAGAAGGTGC | -153 to -46 | SEQ. ID. NO. 19 |
| PAX5mR3 | ACTTCAACCTACGCCGAACG | | SEQ. ID. NO. 20 |
| PAX5uF3 | AGTGTATGTTTTAATAGAAGGTGT | | SEQ. ID. NO. 21 |
| PAX5uR3 | AACTTCAACCTACACCAAACA | | SEQ. ID. NO. 22 |

TABLE 1.2

Target sequences used in this study

1) SEQ. ID. NO. 11:
Sequence of promoter region of human PAX5 gene
(-248 to -144 from the transcription start site)

AAACAAAAACCCGGCCTGCGCTCGTCTAAGCAGCGGGGTTTGCACATGGA

GATGTCACAGGCCCCGCGCACAGCGCAGAGGGCCGCGACCCCCAAGCGCA

TGTCT

2) SEQ. ID. NO. 12:
PAX5 protein coding cDNA sequence (1176 bp)

ATGGATTTAGAGAAAAATTATCCGACTCCTCGGACCAGCAGGACAGGACA

TGGAGGAGTGAATCAGCTTGGGGGGGTTTTTGTGAATGGACGGCCACTCC

CGGATGTAGTCCGCCAGAGGATAGTGGAACTTGCTCATCAAGGTGTCAGG

CCCTGCGACATCTCCAGGCAGCTTCGGGTCAGCCATGGTTGTGTCAGCAA

AATTCTTGGCAGGTATTATGAGACAGGAAGCATCAAGCCTGGGGTAATTG

GAGGATCCAAACCAAAGGTCGCCACACCCAAAGTGGTGGAAAAAATCGCT

GAATATAAACGCCAAAATCCCACCATGTTTGCCTGGGAGATCAGGGACCG

GCTGCTGGCAGAGCGGGTGTGTGACAATGACACCGTGCCTAGCGTCAGTT

CCATCAACAGGATCATCCGGACAAAAGTACAGCAGCCACCCAACCAACCA

GTCCCAGCTTCCAGTCACAGCATAGTGTCCACTGGCTCCGTGACGCAGGT

GTCCTCGGTGAGCACGGATTCGGCCGGCTCGTCGTACTCCATCAGCGGCA

TCCTGGGCATCACGTCCCCAGCGCCGACACCAACAAGCGCAAGAGAGAC

GAAGGTATTCAGGAGTCTCCGGTGCCGAACGGCCACTCGCTTCCGGGCAG

AGACTTCCTCCGGAAGCAGATGCGGGGAGACTTGTTCACACAGCAGCAGC

TGGAGGTGCTGGACCGCGTGTTTGAGAGGCAGCACTACTCAGACATCTTC

ACCACCACAGAGCCCATCAAGCCCGAGCAGACCACAGAGTATTCAGCCAT

GGCCTCGCTGGCTGGTGGGCTGGACGACATGAAGGCCAATCTGGCCAGCC

CCACCCCTGCTGACATCGGGAGCAGTGTGCCAGGCCCGCAGTCCTACCCC

ATTGTGACAGGCCGTGACTTGGCGAGCACGACCCTCCCCGGGTACCCTCC

ACACGTCCCCCCGCTGGACAGGGCAGCTACTCAGCACCGACGCTGACAG

GGATGGTGCCTGGGAGTGAGTTTTCCGGGAGTCCCTACAGCCACCCTCAG

TATTCCTCGTACAACGACTCCTGGAGGTTCCCCAACCCGGGGCTGCTTGG

CTCCCCCTACTATTATAGCGCTGCCGCCCGAGGAGCCGCCCCACCTGCAG

CCGCCACTGCCTATGACCGTCACTGA

3) SEQ. ID. NO. 13:
PAX5 full length cDNA sequence (Genbank:
NM_016734, 3650 bp)

AGCACTGCTGCTCTCCCGGCTTCCCGCTCTACTCCGGCCGGGCCGGGTCC

GCCACGTCTGGCGCGCTGAGCAGGCCCGGCCGCGCAGCGCCTACCCTTTC

CTCGCTCCGGGCCGGCAGTGTGGGGCGGCGCGCTGGGGGCGCGGCGTGTC

TGGGGACATCTTGTGATGTTGGCGAGAACAGGACATGATCTCACATGGCG

AGAAGCTCTTTAGTTCCTTAATCATTTCACGGTGCCTTCGGACGCTTTTT

TTCCACCTAAAACGTTTAGTTTCAGCTCAGTGATCAGCTACCCCAGCTCG

GCGGGGGAGCGGAAGGCTTGAATTATTCCGACCTGTGAGCGGCCCCTGGC

ACCAAAAAAAAAAAAAAAAAAAAAAAAAAGAAAAAAAAAGGCACAAAA

AAGTGGAAACTTTTCCCTGTCCATTCCATCAAGTCCTGAAAAATCAAAAT

GGATTTAGAGAAAAATTATCCGACTCCTCGGACCAGCAGGACAGGACATG

GAGGAGTGAATCAGCTTGGGGGGGTTTTTGTGAATGGACGGCCACTCCCG

GATGTAGTCCGCCAGAGGATAGTGGAACTTGCTCATCAAGGTGTCAGGCC

CTGCGACATCTCCAGGCAGCTTCGGGTCAGCCATGGTTGTGTCAGCAAAA

TTCTTGGCAGGTATTATGAGACAGGAAGCATCAAGCCTGGGGTAATTGGA

GGATCCAAACCAAAGGTCGCCACACCCAAAGTGGTGGAAAAAATCGCTGA

ATATAAACGCCAAAATCCCACCATGTTTGCCTGGGAGATCAGGGACCGGC

TGCTGGCAGAGCGGGTGTGTGACAATGACACCGTGCCTAGCGTCAGTTCC

ATCAACAGGATCATCCGGACAAAAGTACAGCAGCCACCCAACCAACCAGT

CCCAGCTTCCAGTCACAGCATAGTGTCCACTGGCTCCGTGACGCAGGTGT

CCTCGGTGAGCACGGATTCGGCCGGCTCGTCGTACTCCATCAGCGGCATC

CTGGGCATCACGTCCCCCAGCGCCGACACCAACAAGCGCAAGAGAGACGA

AGGTATTCAGGAGTCTCCGGTGCCGAACGGCCACTCGCTTCCGGGCAGAG

ACTTCCTCCGGAAGCAGATGCGGGGAGACTTGTTCACACAGCAGCAGCTG

GAGGTGCTGGACCGCGTGTTTGAGAGGCAGCACTACTCAGACATCTTCAC

CACCACAGAGCCCATCAAGCCCGAGCAGACCACAGAGTATTCAGCCATGG

CCTCGCTGGCTGGTGGGCTGGACGACATGAAGGCCAATCTGGCCAGCCCC

ACCCCTGCTGACATCGGGAGCAGTGTGCCAGGCCCGCAGTCCTACCCCAT

TGTGACAGGCCGTGACTTGGCGAGCACGACCCTCCCCGGGTACCCTCCAC

ACGTCCCCCCGCTGGACAGGGCAGCTACTCAGCACCGACGCTGACAGGG

ATGGTGCCTGGGAGTGAGTTTTCCGGGAGTCCCTACAGCCACCCTCAGTA

TTCCTCGTACAACGACTCCTGGAGGTTCCCCAACCCGGGGCTGCTTGGCT

CCCCCTACTATTATAGCGCTGCCGCCCGAGGAGCCGCCCCACCTGCAGCC

GCCACTGCCTATGACCGTCACTGACCCTTGGAGCCAGGCGGGCACCAAAC

ACTGATGGCACCTATTGAGGGTGACAGCCACCCAGCCCTCCTGAAGATAG

CCAGAGAGCCCATGAGACCGTCCCCCAGCATCCCCCACTTGCCTGAAGCT

CCCCTCTTCCTCTCTTCCTCCAGGGACTCTGGGGCCCTTTGGTGGGGCCG

TTGGACTTCTGGATGCTTGTCTATTTCTAAAAGCCAATCTATGAGCTTCT

CCCGATGGCCACTGGGTCTCTGCAAACCAATAGACTGTCCTGCAAATAAC

CGCAGCCCCAGCCCAGCCTGCCTGTCCTCCAGCTGTCTGACTATCCATCC

ATCATAACCACCCCAGCCTGGGAAGGAGAGCTTGCTTTTGTTGCTTCAGC

AGCACCCATGTAAATACCTTCTTGCTTTTCTGTGGGCCTGAAGGTCCGAC

TGAAGACTGCTCCACCCATGATGCATCTCGCACTCTTGGTGCATCACC

GGACATCTTAGACCTATGGCAGAGCATCCTCTCTGCCCTGGGTGACCCTG

GCAGGTGCGCTCAGAGCTGTCCTCAAGATGGAGGATGCTGCCCTTGGGCC

CCAGCCTCCTGCTCATCCCTCCTTCTTTAGTATCTTTACGAGGAGTCTCA

CTGGGCTGGTTGTGCTGCAGGCTCCCCCTGAGGCCCCTCTCCAAGAGGAG

TABLE 1.2-continued

Target sequences used in this study

CACACTTTGGGGAGATGTCCTGGTTTCCTGCCTCCATTTCTCTGGGACCG

ATGCAGTATCAGCAGCTCTTTTCCAGATCAAAGAACTCAAAGAAAACTGT

CTGGGAGATTCCTCAGCTACTTTTCCGAAGCAGAATGTCATCCGAGGTAT

TGATTACATTGTGGACTTTGAATGTGAGGGCTGGATGGGACGCAGGAGAT

CATCTGATCCCAGCCAAGGAGGGGCCTGAGGCTCTCCCTACTCCCTCAGC

CCCTGGAACGGTGTTTTCTGAGGCATGCCCAGGTTCAGGTCACTTCGGAC

ACCTGCCATGGACACTTCACCCACCCTCCAGGACCCCAGCAAGTGGATTC

TGGGCAAGCCTGTTCCGGTGATGTAGACAATAATTAACACAGAGGACTTT

CCCCCACACCCAGATCACAAACAGCCTACAGCCAGAACTTCTGAGCATCC

TCTCGGGGCAGACCCTCCCCGTCCTCGTGGAGCTTAGCAGGCAGCTGGGC

ATGGAGGTGCTGGGGCTGGGGCAGATGCCTAATTTCGCACAATGCATGCC

CACCTGTTGATCTAAGGGGCCGCGATGGTCAGGGCCACGGCCAAGGGCCA

CGGGAACTTGGAGAGGGAGCTTGGAGAACTCACTGTGGGCTAGGGTGGTC

AGAGGAAGCCAGCAGGGAAGATCTGGGGGACAGAGGAAGGCCTCCTGAGG

GAGGGGCAGGAGAGCAGTGAGGAGCTGCTGTGTGACCTGGGAGTGATTTT

GACATGGGGGTGCCAGGTGCCATCATCTCTTTACCTGGGGCCTTAATTCC

TTGCATAGTCTCTCTTGTCAAGTCAGAACAGCCAGGTAGAGCCCTTGTCC

AAACCTGGGCTGAATGACAGTGATGAGAGGGGGCTTGGCCTTCTTAGGTG

ACAATGTCCCCCATATCTGTATGTCACCAGGATGGCAGAGAGCCAGGGCA

GAGAGAGACTGGACTTGGGATCAGCAGGCCAGGCAGGTCTTGTCCTGGTC

CTGGCCACATGTCTTTGCTGTGGGACCTCAGACAAAACCCTGCACCTCTT

TGAGCCTTGGCTGCCTTGGTGCAGCAGGGTCATCTGTAGGGCCACCCCAC

AGCTCTTTCCTTCCCCTCCTCTCTCCAGGGAGCCGGGGCTGTGAGAGGAT

CATCTGGGGCAGGCCCTCCACTTCCAAGCAAGCAGATGGGGGTGGGCACC

TGAGGCCCAATAATATTTGGACCAAGTGGGAAACAAGAACACTCGGAGGG

GCGGGAATCAGAAGAGCCTGGAAAAAGACCTAGCCCAACTTCCCTTGTGG

GAAACTGAGGCCCAGCTTGGGGAAGGCCAGGACCATGCAGGGAGAAAAAG

4) SEQ. ID. NO. 14:
Partial coding sequence used to detect human
PAX5 mRNA (230 bp).

GTCCATTCCATCAAGTCCTGAAAAATCAAAATGGATTTAGAGAAAAATTA

TCCGACTCCTCGGACCAGCAGGACAGGACATGGAGGAGTGAATCAGCTTG

GGGGGGTTTTTGTGAATGGACGGCCACTCCCGGATGTAGTCCGCCAGAGG

ATAGTGGAACTTGCTCATCAAGGTGTCAGGCCCTGCGACATCTCCAGGCA

GCTTCGGGTCAGCCATGGTTGTGTCAGCAA

5) SEQ. ID. NO. 23
PAX5_HUMAN Paired box protein Pax-5, 391 amino
acids

MDLEKNYPTPRTSRTGHGGVNQLGGVFVNGRPLPDVVRQRIVELAHQGVR

PCDISRQLRVSHGCVSKILGRYYETGSIKPGVIGGSKPKVATPKVVEKIA

EYKRQNPTMFAWEIRDRLLAERVCDNDTVPSVSSINRIIRTKVQQPPNQP

VPASSHSIVSTGSVTQVSSVSTDSAGSSYSISGILGITSPSADTNKRKRD

EGIQESPVPNGHSLPGRDFLRKQMRGDLFTQQQLEVLDRVFERQHYSDIF

TTTEPIKPEQTTEYSAMASLAGGLDDMKANLASPTPADIGSSVPGPQSYP

IVTGRDLASTTLPGYPPHVPPAGQGSYSAPTLTGMVPGSEFSGSPYSHPQ

YSSYNDSWRFPNPGLLGSPYYYSAAARGAAPPAAATAYDRH

6) SEQ. ID. NO. 24
Sequence of promoter region of PAX5 gene
(-352 to -46 from the transcription start site)

TGAATCGGAGTAAACCGGAACGTCGCCTCGGTGCCTGGCAACACTGCCAG

CCTTTGCAACCCCTTTCAAAAGCACCTGCTTGGCCGAGCAGTTAATTTCT

TCAAAAACAAAAACCCGGCCTGCGCTCGTCTAAGCAGCGGGGTTTGCACA

TGGAGATGTCACAGGCCCCGCGCACAGCGCAGAGGGCCGCGACCCCCAAG

CGCATGTCTTAATAGAAGGTGCGGCTGGAAGACCCGGGCTCCCGGGCTCC

GCTTCGGTCTGCCCCTTCCCGTAGGTGCGCTGGCTAGCGCCCGGCGCAGG

CTGAAGC

2. Results

2.1 Data Mining for PAX5 Gene

2.1.1 PAX5

PAX5 is a member of PAX transcription factor gene family. Using University of California Santa Cruz Genome Bioinformatics (UCSC) database, we obtained the information that PAX5 gene was located at chromosome 9p13.2. Two transcript variants have been reported at this location (Busslinger, Klix et al., 1996). The second variant did not contain the paired box domain, which played an essential role in transcriptional activity, so we did not discuss it in this study. PAX5 encodes a transcription factor which has 391 amino acids.

2.1.2 PAX5 CpG Island

Using CpG Island Searcher, we could identify a CpG island spanned the promoter region and the first exon: GC content, 59.4%; observed/expected CpG ratio, 0.885; 79 CpG sites in a 1014 bp region. We designed the MSP primers and BGS primers according to the CpG island analysis result (FIG. 1 and Table 1.1). FIG. 1 shows the promoter region and part of the first exon of PAX5. Transcription starting site is marked as TSS. The MSP region, BGS region and the 10 CpG sites within the BGS region are also presented.

2.2 PAX5 Gene Expression

2.2.1 PAX5 is Expressed in Most of Human Tissues

To determine the expression profile of PAX5, we examined the PAX5 expression level in human normal adult and fetal tissues. Using semi-quantitative RT-PCR, PAX5 was found to be expressed in most of the human tissues and fetal tissues, especially in digestion organs like liver, kidney, spleen, pancreas, larynx, trachea, lung, breast, cervix, gone marrow and lymph nodes, esophagus, stomach, colon and rectum.

2.2.2 PAX5 is Epigenetically Suppressed in Cancer Cell Lines

Figure 2:
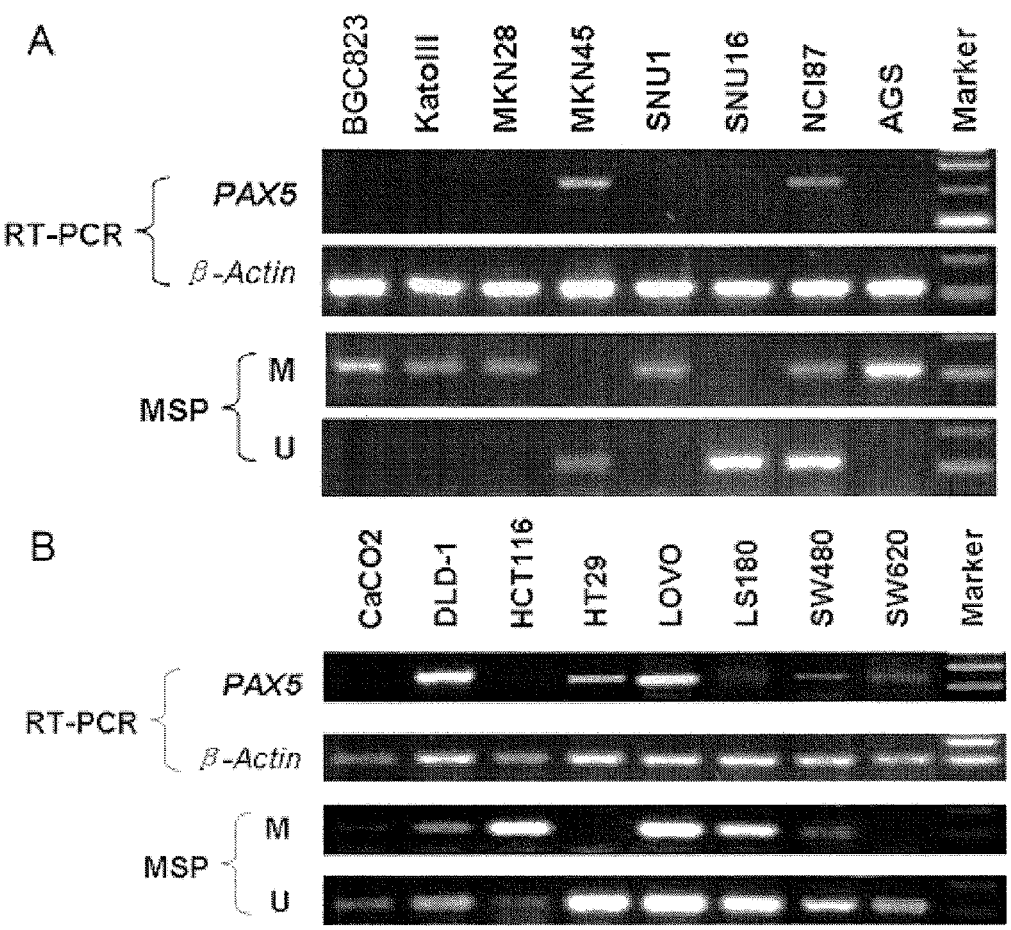
FIG. 2 Shows PAX 5 mRNA expression in cell lines in an embodiment.

To characterize epigenetic effectors of PAX5 in GC, we detected expression level and methylation status of PAX5 gene in 8 GC cell lines and 8 CRC cell lines. FIG. 2 shows PAX5 mRNA expression and promoter methylation in (A) GC cell lines (B) CRC cell lines. The mRNA expression of PAX5 in cell lines was determined by RT-PCR. Amplification of β-Actin was performed as an internal control for RNA quality. MSP was performed to detect the methylation status. (M: bands amplified by methylation primers, U: bands amplified by unmethylation primers)

For GC cell lines, PAX5 gene was silenced in 6 cell lines (KatoIII, MKN28, SNU1, SNU16, AGS and BGC823) and down-regulated in NCI87 (FIG. 2A). PAX5 transcription was silenced or down-regulated in 7/8 (87.5%) of GC cell lines. For CRC cell lines, loss of expression was detected in 2 cell lines (Caco2 and HCT116) and down-regulation was detected in 4 cell lines (HT29, Ls180, SW480 and SW620), with transcriptional silence or down-regulation were detected in 6/8 (75%) of CRC cell lines (FIG. 2B).

To assess whether the silence or down-regulation of PAX5 could match the methylation status of the promoter region, MSP was performed using methylation specific primers and unmethylation specific primers. MSP amplicon covered the region of −248 bp~−144 bp relative to TSS. Full methylation was detected in 5 GC cell lines (KatoIII, MKN28, SNU1, AGS and BGC823), and partial methylation was found in 1 GC cell line (NCI87). The methylation status in GC cell lines matched the expression level well except for SNU16 cell line, in which PAX5 was silenced but no methylation was detected. This may due to the reason that PAX5 gene in SNU16 is silenced by other mechanisms such as histone modification or up-steam transcriptional regulation. Partial methylation was also detected in 6 CRC cell lines (Caco2, DLD1, HCT116, LoVo, LS180 and SW480) which displayed silence or down-regulation of PAX5 gene (FIG. 2B).

2.2.3 PAX5 Expression could be Restored after Demethylation Treatment

Figure 3:
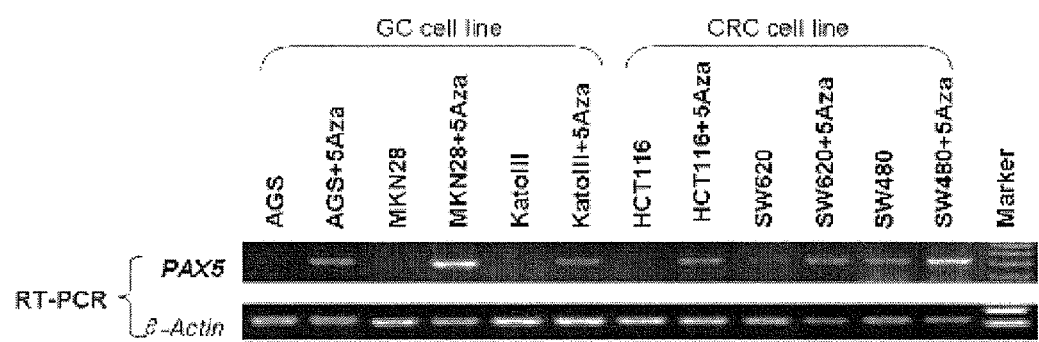
FIG. 3 Shows the effect of a demethylating agent on PAX 5 expression in an embodiment.

To confirm that PAX5 expression was repressed by promoter methylation, 5-Aza was used to pharmacologically interfere with promoter methylation in methylated cell lines of AGS, MKN28, KatoIII, HCT116, SW620 and SW480. FIG. 3 shows PAX5 gene expression in 5-Aza demethylation treated GC and CRC cell lines as determined by RT-PCR. As shown in FIG. 3, 5-Aza treatment could restore expression of all these cell lines, conferring promoter methylation contributes to the epigenetic suppression of PAX5 in GC and CRC cell lines.

2.2.4 PAX5 Expression in Paired Cancer and Adjacent Normal Samples

Figure 4:
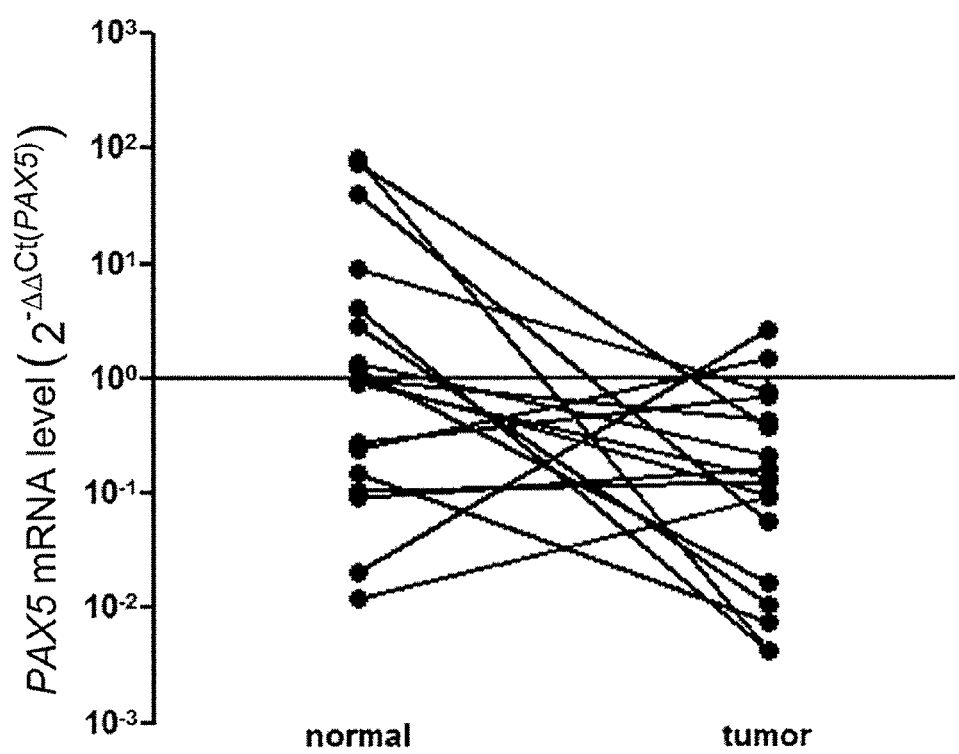
FIG. 4 Shows the relative PAX 5 expression level in paired samples of gastric cancer cells and adjacent normal tissues in an embodiment.

To evaluate the clinical significance of PAX5 gene in primary tumors, we compared the mRNA expression level of PAX5 in 18 pairs of GC biopsies and their adjacent non-tumor tissues using qPCR. FIG. 4 shows PAX5 gene relative expression level in paired GC samples. Relative mRNA level of PAX5 was presented by $Lg(2^{-\Delta\Delta Ct(PAX5)})$. Totally, PAX5 expression in 18 pairs of GC with their corresponding adjacent non-cancerous tissues were quantified by qPCR. The dots for each paired samples were connected with a line. P values were calculated with paired T test.

Compared with the adjacent normal tissues, PAX5 was significantly down-regulated in GC tissues (P=0.0196) (FIG. 4A).

2.3 Funtional Assay 2.3.1 Transfection Using Vector with Green Fluorescent Protein (GFP)

To check the transfection efficiency, pcDNA3.1-eGFP was transfected into cell lines. The transient transfection efficiency was about 40%~50% for AGS, and >80% for HCT116. In this regard, the transient transfection of HCT116 was used directly for functional assays. Stable transfection of PAX5 had to be established by using 2 to 3 weeks of G418 selection for AGS due to the low transient transfection efficiency. BGC823 with stable PAX5 transfection was used in the in vivo tumorigenicity assay for long-term action.

2.3.2 PAX5 was Over-Expressed in the Transfected Cell Lines

Figure 5:
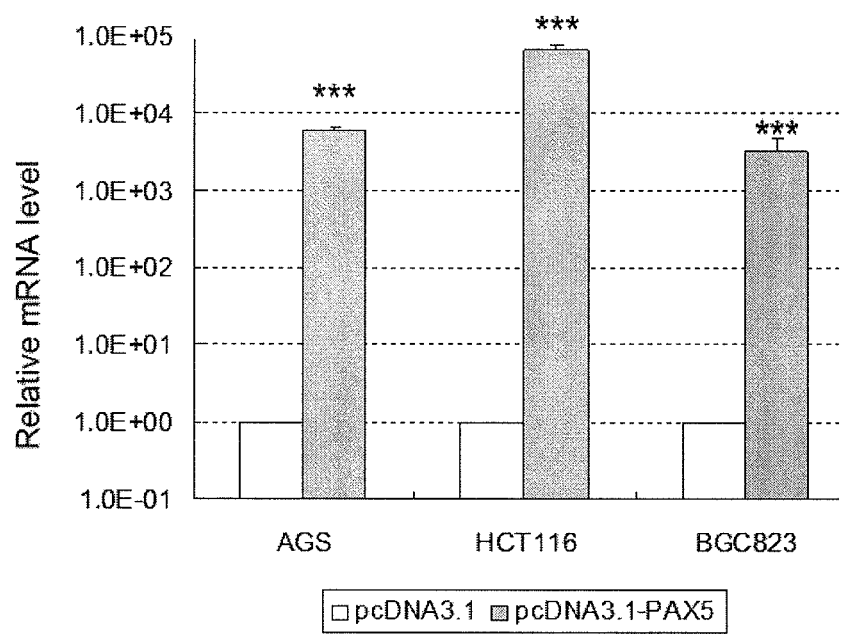
FIG. 5 Shows the relative levels of PAX 5 mRNA in transfected cell lines in an embodiment.

Three cell lines (AGS, BGC823 and HCT116), whose PAX5 gene was silenced and fully methylated, were chosen to perform the biological function assay. PAX5 mRNA level was detected in the stable transfection cell lines AGS, BGC823 and transient transfection cell line HCT116 by using qPCR. FIG. 5 shows relative mRNA levels in transfected cell lines. The expression level in control cell line was defined as 1. The relative fold was calculated as $2^{(Ctcontrol-CtPAX5)}$. (*** P value of t test is less than 0.0001). As shown in FIG. 5, cells transfected with pcDNA3.1-PAX5 had thousands folds of more PAX5 mRNA than cells transfected with empty vector (pcDNA3.1). In keeping with the enhanced mRNA level, protein expression of PAX5 was also up-regulated in PAX5 transfected cell lines as determined by western blot.

2.3.3 Inhibition of Cell Proliferation by PAX5

Figure 6:
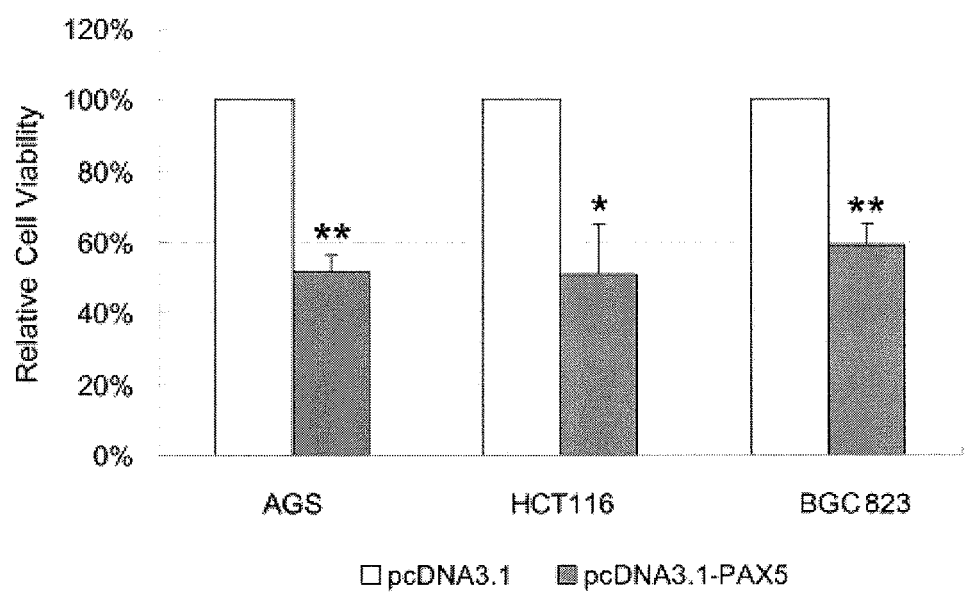
FIG. 6 Shows exogenous PAX 5 expression in cells in an embodiment.
Figure 7:
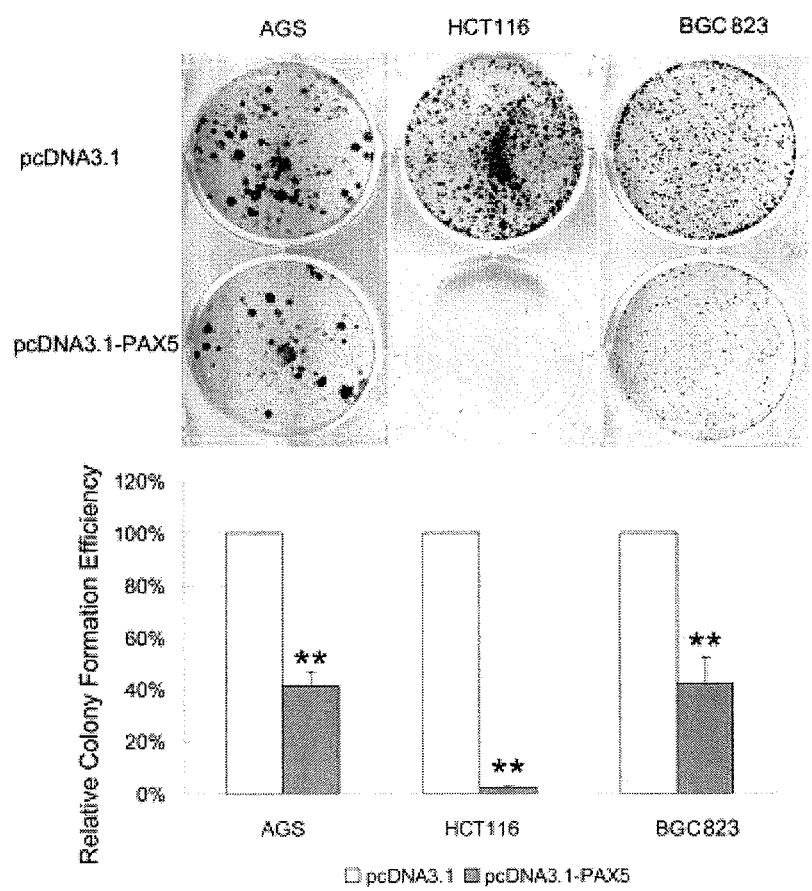
FIG. 7 Shows the effect of PAX 5 expression on transfected cells in Colony formation assay on an embodiment.

In vitro biological effects of PAX5 on cell growth in the PAX5 non-expressing cell lines (AGS, HCT116 and BGC823) were examined by cell viability assay and colony formation assay. MTS assay was used for measuring the cell viability. FIG. 6 shows relative cell viability as mean of absorbance±SD from three independent experiments. Histogram represents relative percentage of cell viability. (* P value of t test is less than 0.05;  P value is less than 0.01.). In the cell lines with PAX5 over-expression, cell viabilities were significantly inhibited to 52% (AGS, P=0.0034), 51% (HCT116, P=0.0277) and 59% (BGC823, P=0.0066), compared to control cells (100%). In addition, after transfection of PAX5, cell growth was significantly suppressed to 41% (AGS, P=0.0028), 2% (HCT116, P<0.0001) and 42% (BGC823, P=0.0090), compared with the control cells (100%). This is shown in FIG. 7 which shows the results of a Colony Formation Assay on cell lines transfected with PAX5 as compared to control transfections. Quantitative analyses of colony numbers are shown as values of mean±SD (standard deviation) from three independent experiments. Histogram represents relative percentage of number of colony. ( P value of t test is less than 0.01.) Both colony formation and MTS assay solidly demonstrated that PAX5 could inhibit cell growth of GC cells in vitro.

2.3.4 PAX5 Caused Cell Cycle Arrest in G1 Phase

To determine the influence of PAX5 on cell cycle distribution, both AGS/PAX5 and AGS/pcDNA3.1 was stained with PI. Cell numbers in different phases of cell cycle were counted by FACScan. The cell proportion in G1 phase of cells transfected with AGS/pcDNA3.1 was 49.2%±1.5%, while the proportion in G1 phase of cells transfected with AGS/PAX5 was 58.6%±2.6%. The proportion in AGS/PAX5 was statistically significantly higher compared with the control group (P=0.0055).

2.3.5 Induction of Cell Apoptosis by PAX5

To determine if the PAX5 mediated growth inhibition was the result of apoptosis, cell apoptosis was determined by annexin-V-FITC/PI FACs analysis. The results demonstrated an increase in the numbers of early apoptotic cells (5.60%±0.75% vs. 2.87%±0.38%, P=0.0316) in AGS stably transfected with PAX5 in comparison to vector controls. The numbers of dead and late apoptotic cells did not show significant difference between these two groups (P>0.10)

TUNEL staining was performed to validate the apoptosis induced by PAX5 in the cancer tissue from nude mice. Consistent with the result in annexin-V-FITC/PI FACs analysis, percentage of TUNEL-positive cell was higher in PAX5 expressed tissues compared with the vector controls (3.62%±1.12% vs. 1.54%±0.71%, P=0.0080).

2.3.6 PAX5 Inhibits GC Cell Migration and Invasion

To investigate the effect of PAX5 in cancer cell metastasis and invasiveness, the monolayer wound-healing assay was performed. A delay in the closure of the wound gaps for AGS/PAX5 was observed, compared with control cell AGS/vector.

For the quantitative assessment of cell migration and invasion, we also performed the matrigel invasion assay. The invaded cell number in AGS with PAX5 expression was significantly lower than in control AGS without PAX5 expression (P=0.0218). The result of wound repair assay and matrigel assay suggested that PAX5 gene could suppress the GC cell mobility and invasiveness.

2.3.7 In Vivo Tumor Suppression

Figure 8:
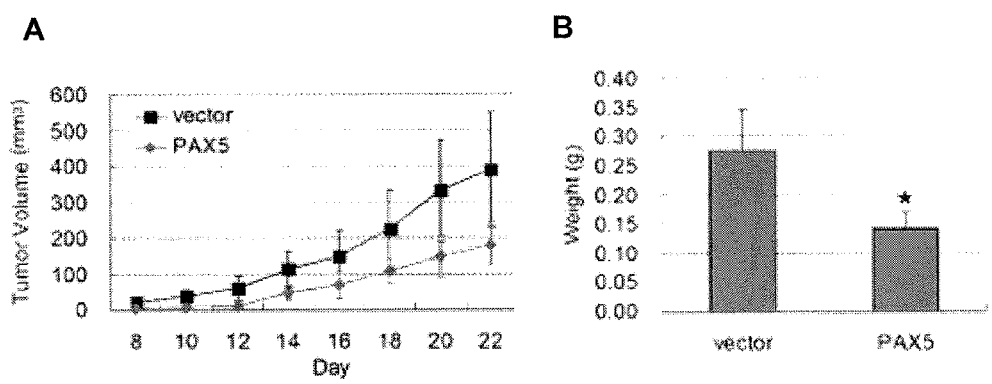
FIG. 8 Shows the methylation percentage of human gastric tissue from tumors and normal in an embodiment.

We randomly injected BGC823/PAX5 or control cell line BGC823/vector into the dorsal flank of nude mice to compare the tumor growth patterns in vivo. Twenty-two days after inoculation, the experiment was terminated and the mice were sacrificed. The tumor growth curve in nude mice was shown in FIG. 8A. The average tumor size was significantly lower in nude mice injected with BGC823/PAX5 as compared with the control mice injected with BGC823/vector (P<0.0001, repeated measures ANOVA) (n=5/group). The tumors were isolated and weighed during harvesting. The tumor tissues from BGC823/PAX5 group was lighter than those from control group (P=0.0112) (FIG. 8B). In FIG. 8B, the histogram represents mean of the tumor weight from the BGC823/PAX5 and BGC823/vector group. * P value of t test is less than 0.05. Immunostaining using specific antibody was performed to confirm the existence of PAX5 protein expression in the tumor tissues from BGC823/PAX5 group and exhibited 20%-30% PAX5 positive cells in this group. However, no PAX5 expression was observed in the tumors of the control group, providing evidence that PAX5 can inhibit the tumor growth in gastric carcinoma.

2.4 Methylation Status in GC Patients

The expression of PAX5 was significantly different in primary tumors and their adjacent non-tumor tissues, and showed correlation with methylation status in cancer cell lines.

2.4.1 Methylation Status at each CpG Site in the BGS Region

BGS was performed to evaluate methylation status at each CpG site within the promoter region shown in FIG. 1. Percentage of partial methylation was roughly calculated by the following formula: Methylation $\% = H_C/(H_C+H_T) \times 100\%$ BGS was performed on 3 GC cell line (AGS, MKN28 and MKN45). Average methylation ratios of AGS, MKN28 and MKN45 were revealed to be 100%, 92% and 8%, respectively (Table 2.2). This completely consistent with the results from MSP assay that demonstrated full methylation in AGS, MKN28 and no methylation in MKN45

TABLE 2.2

Methylation percentage of PAX5 in GC cell lines.

| GC cell | Methylation percentage at each CpG site (%) | | | | | | | | | | Average |
|---|---|---|---|---|---|---|---|---|---|---|---|
| | 1 | 2 | 3 | 4 | 5 | 6 | 7 | 8 | 9 | 10 | |
| AGS | 100 | 100 | 100 | 100 | 100 | 100 | 100 | 100 | 100 | 100 | 100.0 |
| MKN28 | 80 | 80 | 80 | 100 | 90 | 90 | 100 | 100 | 100 | 100 | 92.0 |
| MKN45 | 0 | 0 | 10 | 10 | 10 | 10 | 10 | 10 | 10 | 10 | 8.0 |

BGS was also performed on 19 normal gastric biopsies and 161 GC specimens. The average methylation ratios in normal gastric tissues were ranged from 0% to 39% (Table 2.3). There were 3 samples with methylation percentage more than 10% (15, 27, 39%). The average methylation ratios in GC tissues altered from 0% to 100%.

TABLE 2.3

Methylation percentage of PAX5 in normal gastric tissues.

| Case No. | Gender | Age | Methylation percentage at each CpG site (%) | | | | | | | | | | Average |
|---|---|---|---|---|---|---|---|---|---|---|---|---|---|
| | | | 1 | 2 | 3 | 4 | 5 | 6 | 7 | 8 | 9 | 10 | |
| P009 | M | 64 | 0 | 0 | 0 | 0 | 0 | 0 | 0 | 0 | 0 | 0 | 0.0 |
| P012 | M | 47 | 0 | 0 | 0 | 0 | 0 | 0 | 0 | 0 | 0 | 0 | 0.0 |
| P024 | F | 19 | 0 | 0 | 0 | 0 | 0 | 0 | 0 | 0 | 0 | 0 | 0.0 |
| P032 | M | 35 | 0 | 0 | 0 | 0 | 0 | 0 | 0 | 0 | 0 | 0 | 0.0 |
| P039 | M | 56 | 0 | 0 | 0 | 0 | 0 | 0 | 0 | 0 | 0 | 0 | 0.0 |
| P050 | M | 51 | 0 | 0 | 0 | 0 | 0 | 0 | 0 | 0 | 0 | 0 | 0.0 |
| P059 | F | 67 | 0 | 0 | 0 | 10 | 10 | 20 | 0 | 10 | 20 | 0 | 7.0 |
| P061 | F | 52 | 0 | 0 | 0 | 0 | 0 | 0 | 0 | 0 | 0 | 0 | 0.0 |
| P065 | F | 46 | 10 | 10 | 10 | 10 | 0 | 0 | 10 | 0 | 0 | 0 | 5.0 |
| P073 | F | 40 | 0 | 0 | 0 | 0 | 0 | 0 | 0 | 0 | 0 | 0 | 0.0 |
| P079 | F | 63 | 0 | 0 | 0 | 0 | 0 | 0 | 0 | 0 | 0 | 0 | 0.0 |
| P081 | F | 41 | 0 | 0 | 0 | 0 | 0 | 0 | 0 | 0 | 0 | 0 | 0.0 |
| P086 | F | 46 | 40 | 50 | 40 | 30 | 30 | 30 | 50 | 30 | 40 | 50 | 39.0 |
| P088 | F | 56 | 0 | 0 | 0 | 0 | 0 | 0 | 0 | 0 | 0 | 0 | 0.0 |
| P105 | M | 82 | 0 | 0 | 0 | 0 | 0 | 0 | 0 | 0 | 0 | 0 | 0.0 |
| P106 | F | 46 | 20 | 10 | 10 | 10 | 10 | 20 | 30 | 20 | 10 | 10 | 15.0 |
| P121 | F | 76 | 20 | 20 | 40 | 20 | 20 | 30 | 40 | 20 | 20 | 40 | 27.0 |

TABLE 2.3-continued

Methylation percentage of PAX5 in normal gastric tissues.

| Case No. | Gender | Age | Methylation percentage at each CpG site (%) | | | | | | | | | | Average |
|---|---|---|---|---|---|---|---|---|---|---|---|---|---|
| | | | 1 | 2 | 3 | 4 | 5 | 6 | 7 | 8 | 9 | 10 | |
| P131 | F | 77 | 0 | 0 | 0 | 0 | 0 | 0 | 0 | 0 | 0 | 0 | 0.0 |
| P133 | M | 22 | 0 | 0 | 0 | 0 | 0 | 0 | 0 | 0 | 0 | 0 | 0.0 |

Figure 9:
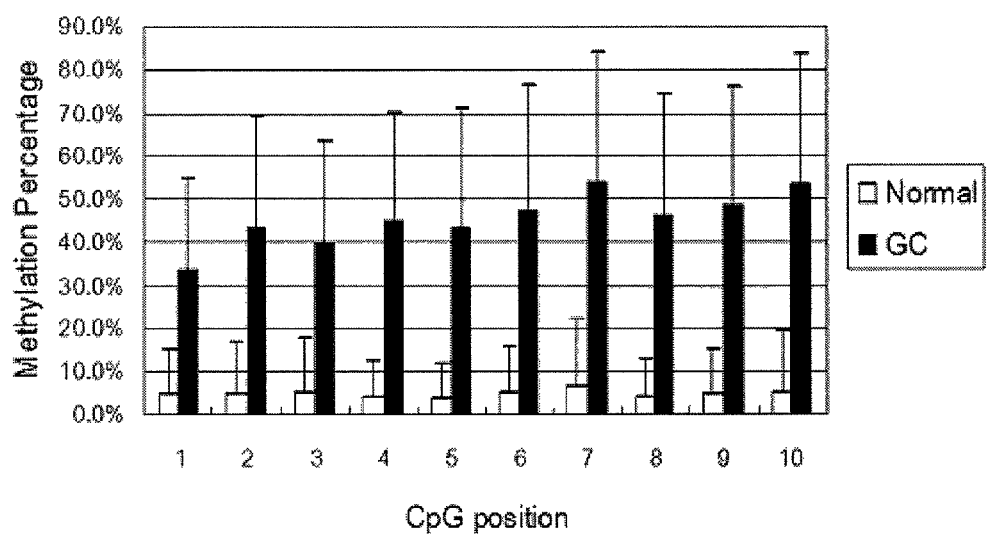
FIG. 9 Shows methylation status of PAX5 CpG islands in cells in an embodiment.

As will be seen from FIG. 9, methylation ratios in normal samples were significantly lower than in GC biopsies (P<0.0001). The difference within the normal group or the GC group was not significant.

2.4.2 Cut Off Value for Distinguishing Methylation and Unmethylation

Figure 10:
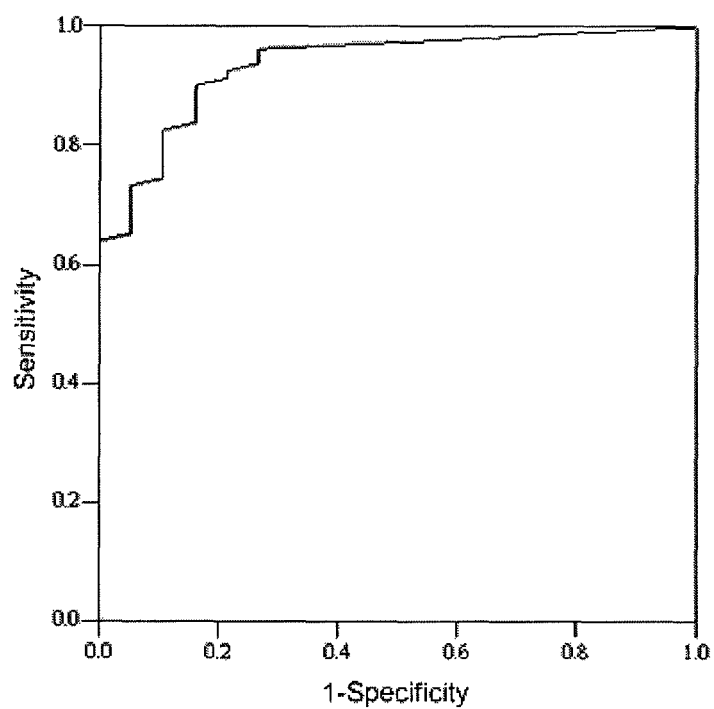
FIG. 10 Shows a Receiver Operating Characteristic (ROC) curve for methylation of PAX5 in an embodiment.

As a biomarker, it was important to determine the methylation status using a cutoff value. ROC curve is a useful tool for organizing classifiers and visualizing their performance. In this study, ROC was used to determine the cutoff value for PAX5 methylation status in patient and the results of the analysis are presented in FIG. 10. In FIG. 10 the area under the ROC Curve (AUC) was 0.937. Considering the balance of sensitivity (90.1%) and specificity (84.2%), 8.5% was chosen as the cutoff value (Methylated sample: methylation %>8.5%, Unmethylated sample: methylation %≥8.5%). Using this cutoff value, 145 of 161 (90.1%) GC samples and 3 of 19 (15.8%) normal samples were methylated.

2.4.3 Association between PAX5 Methylation and Clinical Characteristics

Figure 11:
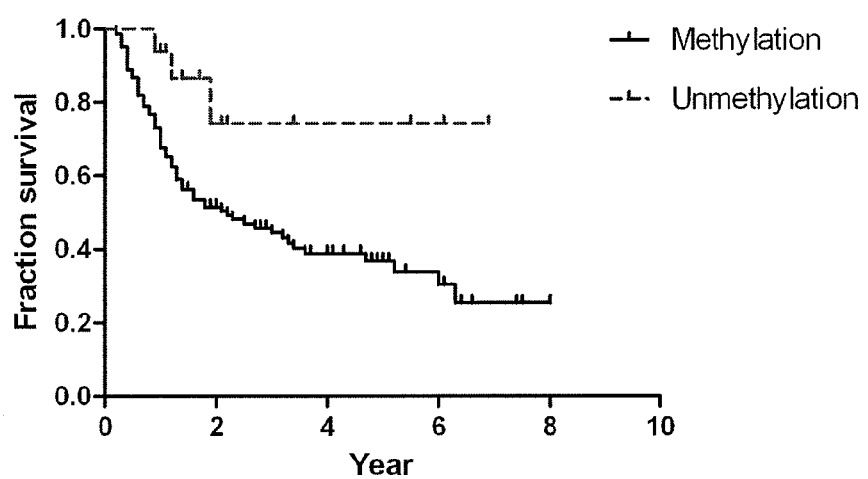
FIG. 11 Shows a Kaplan-Meier analysis of gastric cancer patient survival in an embodiment.

To evaluate the clinical application of PAX5 in gastric tumors, we analyzed the correlation between PAX5 methylation and clinical features including patient age, gender, tumor stage, *H. pylori* infection status, Lauren type, tumor differentiation, and survival data. No statistically significance difference was found with patient age, gender, tumor stage, *H. pylori* infection status, Lauren type, or degree of tumor differentiation. However, patients with PAX5 methylation in tumor tissues (methylation, median survival of 670 days) had poorer survival than others (unmethylation, median survival of 2,205 days). This is shown in FIG. 11 which is a Kaplan Meier graph of survival for gastric cancer patients. This difference is statistically significant based on the log-rank test (P=0.0201, Hazard Ratio=2.212).

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed. Particular embodiments may alternatively comprise or consist of or exclude any one or more of the elements disclosed.

The embodiments of the invention in which an exclusive property or privilege is claimed are defined as follows:

1. A method for detecting DNA methylation, comprising the step of:
   determining, in a gastric mucosa sample taken from a patient, methylation level of a target DNA sequence that is (1) SEQ ID NO:27; or (2) a segment of SEQ ID NO:27 comprising at least 50 consecutive nucleotides of SEQ ID NO:27 and comprising a plurality of CpG base pairs.

2. The method according to claim 1, wherein said determining comprises treating the sample with a reagent that differentially modifies methylated and unmethylated DNA.

3. The method according to claim 2, wherein the target DNA sequence is a segment of at least 50 consecutive nucleotides of SEQ ID NO:26.

4. The method according to claim 1 wherein said determining comprises treating the sample with sodium bisulfite.

5. The method according to claim 2, wherein the determining is performed by COBRA, BGS, or MSP.

6. The method according to claim 1 wherein said determining comprises DNA amplification.

7. The method according to claim 2, wherein the reagent comprises an enzyme that preferentially cleaves unmethylated DNA.

8. The method according to claim 6, wherein said DNA amplification comprises polymerase chain reaction.

9. The method according to claim 1 wherein said detecting uses a primer or probe selected from the group consisting of SEQ ID NOs: 1, 2, 5, 6, 7, 8, 9, 10, 15, 16, 17, 18, 19, 20 and 22.

10. The method of claim 1, wherein the target DNA sequence is SEQ ID NO:26.

11. The method of claim 1, wherein the target DNA sequence is SEQ ID NO:27.

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: synthetic RT-PCR primer PAX5RTF for detecting
      PAX5 mRNA expression

<400> SEQUENCE: 1
gtccattcca tcaagtcctg                                                  20

<210> SEQ ID NO 2
<211> LENGTH: 20
<212> TYPE: DNA
<213> ORGANISM: Artificial Sequence
<220> FEATURE:
<223> OTHER INFORMATION: synthetic RT-PCR primer PAX5RTR for detecting
      PAX5 mRNA expression

<400> SEQUENCE: 2
ttgctgacac aaccatggct                                                  20

```
<210> SEQ ID NO 3
<211> LENGTH: 30
<212> TYPE: DNA
<213> ORGANISM: Artificial Sequence
<220> FEATURE:
<223> OTHER INFORMATION: synthetic cloning primer PAX5CloneF for cloning
      PAX5 protein coding sequence

<400> SEQUENCE: 3
atataagctt gtccattcca tcaagtcctg                                          30

<210> SEQ ID NO 4
<211> LENGTH: 29
<212> TYPE: DNA
<213> ORGANISM: Artificial Sequence
<220> FEATURE:
<223> OTHER INFORMATION: synthetic cloning primer PAX5CloneR for cloning
      PAX5 protein coding sequence

<400> SEQUENCE: 4
atatctcgag agggtcagtg acggtcata                                           29

<210> SEQ ID NO 5
<211> LENGTH: 25
<212> TYPE: DNA
<213> ORGANISM: Artificial Sequence
<220> FEATURE:
<223> OTHER INFORMATION: synthetic BGS primer PAX5BGSF for bisulfite
      genomic sequencing of a CpG island of PAX5

<400> SEQUENCE: 5
gtttttttaa aagtatttgt ttggt                                               25

<210> SEQ ID NO 6
<211> LENGTH: 21
<212> TYPE: DNA
<213> ORGANISM: Artificial Sequence
<220> FEATURE:
<223> OTHER INFORMATION: synthetic BGS primer PAX5BGSR for bisulfite
      genomic sequencing of a CpG island of PAX5

<400> SEQUENCE: 6
gcaccttcta ttaaaacata c                                                   21

<210> SEQ ID NO 7
<211> LENGTH: 23
<212> TYPE: DNA
<213> ORGANISM: Artificial Sequence
<220> FEATURE:
<223> OTHER INFORMATION: synthetic methylation-sensitive PCR (MSP)
      primer PAX5mF2

<400> SEQUENCE: 7
aaataaaaat tcggtttgcg ttc                                                 23

<210> SEQ ID NO 8
<211> LENGTH: 22
<212> TYPE: DNA
<213> ORGANISM: Artificial Sequence
<220> FEATURE:
<223> OTHER INFORMATION: synthetic methylation-sensitive PCR (MSP)
      primer PAX5mR2

<400> SEQUENCE: 8
aaacatacgc ttaaaaatcg cg                                                  22
```

-continued

<210> SEQ ID NO 9
<211> LENGTH: 26
<212> TYPE: DNA
<213> ORGANISM: Artificial Sequence
<220> FEATURE:
<223> OTHER INFORMATION: synthetic methylation-sensitive PCR (MSP)
      primer PAX5uF2

<400> SEQUENCE: 9
taaaaataaa aatttggttt gtgttt                                          26

<210> SEQ ID NO 10
<211> LENGTH: 25
<212> TYPE: DNA
<213> ORGANISM: Artificial Sequence
<220> FEATURE:
<223> OTHER INFORMATION: synthetic methylation-sensitive PCR (MSP)
      primer PAX5uR2

<400> SEQUENCE: 10
ttaaaacata cacttaaaaa tcaca                                           25

<210> SEQ ID NO 11
<211> LENGTH: 105
<212> TYPE: DNA
<213> ORGANISM: Homo sapiens
<220> FEATURE:
<221> NAME/KEY: promoter
<222> LOCATION: (1)...(105)
<223> OTHER INFORMATION: human transcription factor paired box 5 (PAX5,
      paired box homeotic gene 5), B-cell specific activation protein
      (BSAP) B-cell lineage specific activator, B-cell-specific
      transcription factor promoter region -248 to -144

<400> SEQUENCE: 11
aaacaaaaac ccggcctgcg ctcgtctaag cagcggggtt tgcacatgga gatgtcacag     60
gccccgcgca cagcgcagag ggccgcgacc cccaagcgca tgtct                    105

<210> SEQ ID NO 12
<211> LENGTH: 1176
<212> TYPE: DNA
<213> ORGANISM: Homo sapiens
<220> FEATURE:
<223> OTHER INFORMATION: human transcription factor paired box 5 (PAX5,
      paired box homeotic gene 5), B-cell specific activation protein
      (BSAP) B-cell lineage specific activator, B-cell-specific
      transcription factor protein coding cDNA
<220> FEATURE:
<221> NAME/KEY: exon
<222> LOCATION: (1)..(1176)
<223> OTHER INFORMATION: PAX5

<400> SEQUENCE: 12 atg gat tta gag aaa aat tat ccg act cct cgg acc agc agg aca gga      48
Met Asp Leu Glu Lys Asn Tyr Pro Thr Pro Arg Thr Ser Arg Thr Gly
1               5                   10                  15 cat gga gga gtg aat cag ctt ggg ggg gtt ttt gtg aat gga cgg cca      96
His Gly Gly Val Asn Gln Leu Gly Gly Val Phe Val Asn Gly Arg Pro
            20                  25                  30 ctc ccg gat gta gtc cgc cag agg ata gtg gaa ctt gct cat caa ggt     144
Leu Pro Asp Val Val Arg Gln Arg Ile Val Glu Leu Ala His Gln Gly
        35                  40                  45 gtc agg ccc tgc gac atc tcc agg cag ctt cgg gtc agc cat ggt tgt     192
Val Arg Pro Cys Asp Ile Ser Arg Gln Leu Arg Val Ser His Gly Cys
    50                  55                  60 gtc agc aaa att ctt ggc agg tat tat gag aca gga agc atc aag cct     240
Val Ser Lys Ile Leu Gly Arg Tyr Tyr Glu Thr Gly Ser Ile Lys Pro
65                  70                  75                  80

```
ggg gta att gga gga tcc aaa cca aag gtc gcc aca ccc aaa gtg gtg          288
Gly Val Ile Gly Gly Ser Lys Pro Lys Val Ala Thr Pro Lys Val Val
                85                  90                  95 gaa aaa atc gct gaa tat aaa cgc caa aat ccc acc atg ttt gcc tgg          336
Glu Lys Ile Ala Glu Tyr Lys Arg Gln Asn Pro Thr Met Phe Ala Trp
            100                 105                 110 gag atc agg gac cgg ctg ctg gca gag cgg gtg tgt gac aat gac acc          384
Glu Ile Arg Asp Arg Leu Leu Ala Glu Arg Val Cys Asp Asn Asp Thr
        115                 120                 125 gtg cct agc gtc agt tcc atc aac agg atc atc cgg aca aaa gta cag          432
Val Pro Ser Val Ser Ser Ile Asn Arg Ile Ile Arg Thr Lys Val Gln
130                 135                 140 cag cca ccc aac caa cca gtc cca gct tcc agt cac agc ata gtg tcc          480
Gln Pro Pro Asn Gln Pro Val Pro Ala Ser Ser His Ser Ile Val Ser
145                 150                 155                 160 act ggc tcc gtg acg cag gtg tcc tcg gtg agc acg gat tcg gcc ggc          528
Thr Gly Ser Val Thr Gln Val Ser Ser Val Ser Thr Asp Ser Ala Gly
                165                 170                 175 tcg tcg tac tcc atc agc ggc atc ctg ggc atc acg tcc ccc agc gcc          576
Ser Ser Tyr Ser Ile Ser Gly Ile Leu Gly Ile Thr Ser Pro Ser Ala
            180                 185                 190 gac acc aac aag cgc aag aga gac gaa ggt att cag gag tct ccg gtg          624
Asp Thr Asn Lys Arg Lys Arg Asp Glu Gly Ile Gln Glu Ser Pro Val
        195                 200                 205 ccg aac ggc cac tcg ctt ccg ggc aga gac ttc ctc cgg aag cag atg          672
Pro Asn Gly His Ser Leu Pro Gly Arg Asp Phe Leu Arg Lys Gln Met
210                 215                 220 cgg gga gac ttg ttc aca cag cag cag ctg gag gtg ctg gac cgc gtg          720
Arg Gly Asp Leu Phe Thr Gln Gln Gln Leu Glu Val Leu Asp Arg Val
225                 230                 235                 240 ttt gag agg cag cac tac tca gac atc ttc acc acc aca gag ccc atc          768
Phe Glu Arg Gln His Tyr Ser Asp Ile Phe Thr Thr Thr Glu Pro Ile
                245                 250                 255 aag ccc gag cag acc aca gag tat tca gcc atg gcc tcg ctg gct ggt          816
Lys Pro Glu Gln Thr Thr Glu Tyr Ser Ala Met Ala Ser Leu Ala Gly
            260                 265                 270 ggg ctg gac gac atg aag gcc aat ctg gcc agc ccc acc cct gct gac          864
Gly Leu Asp Asp Met Lys Ala Asn Leu Ala Ser Pro Thr Pro Ala Asp
        275                 280                 285 atc ggg agc agt gtg cca ggc ccg cag tcc tac ccc att gtg aca ggc          912
Ile Gly Ser Ser Val Pro Gly Pro Gln Ser Tyr Pro Ile Val Thr Gly
290                 295                 300 cgt gac ttg gcg agc acg acc ctc ccc ggg tac cct cca cac gtc ccc          960
Arg Asp Leu Ala Ser Thr Thr Leu Pro Gly Tyr Pro Pro His Val Pro
305                 310                 315                 320 ccc gct gga cag ggc agc tac tca gca ccg acg ctg aca ggg atg gtg         1008
Pro Ala Gly Gln Gly Ser Tyr Ser Ala Pro Thr Leu Thr Gly Met Val
                325                 330                 335 cct ggg agt gag ttt tcc ggg agt ccc tac agc cac cct cag tat tcc         1056
Pro Gly Ser Glu Phe Ser Gly Ser Pro Tyr Ser His Pro Gln Tyr Ser
            340                 345                 350 tcg tac aac gac tcc tgg agg ttc ccc aac ccg ggg ctg ctt ggc tcc         1104
Ser Tyr Asn Asp Ser Trp Arg Phe Pro Asn Pro Gly Leu Leu Gly Ser
        355                 360                 365 ccc tac tat tat agc gct gcc gcc cga gga gcc gcc cca cct gca gcc         1152
Pro Tyr Tyr Tyr Ser Ala Ala Ala Arg Gly Ala Ala Pro Pro Ala Ala
370                 375                 380 gcc act gcc tat gac cgt cac tga                                          1176
Ala Thr Ala Tyr Asp Arg His
385                 390
```

```
<210> SEQ ID NO 13
<211> LENGTH: 3650
<212> TYPE: DNA
<213> ORGANISM: Homo sapiens
<220> FEATURE:
<223> OTHER INFORMATION: human transcription factor paired box 5 (PAX5,
      paired box homeotic gene 5), B-cell specific activation protein
      (BSAP) B-cell lineage specific activator, B-cell-specific
      transcription factor full length cDNA
<220> FEATURE:
<221> NAME/KEY: exon
<222> LOCATION: (449)..(1624)
<223> OTHER INFORMATION: PAX5

<400> SEQUENCE: 13
agcactgctg ctctcccggc ttcccgctct actccggccg ggccgggtcc gccacgtctg      60
gcgcgctgag caggcccggc cgcgcagcgc ctacccttc ctcgctccgg gccggcagtg     120
tggggcggcg cgctggggc gcggcgtgtc tggggacatc ttgtgatgtt ggcgagaaca     180
ggacatgatc tcacatggcg agaagctctt tagttcctta atcatttcac ggtgccttcg     240 gacgctttt ttccacctaa aacgtttagt ttcagctcag tgatcagcta ccccagctcg     300 gcggggagc ggaaggcttg aattattccg acctgtgagc ggcccctggc accaaaaaaa     360
aaaaaaaaaa aaaaaaaaaa agaaaaaaaa aggcacaaaa aagtggaaac ttttccctgt     420
ccattccatc aagtcctgaa aaatcaaa atg gat tta gag aaa aat tat ccg       472
                                 Met Asp Leu Glu Lys Asn Tyr Pro
                                  1               5 act cct cgg acc agc agg aca gga cat gga gga gtg aat cag ctt ggg      520
Thr Pro Arg Thr Ser Arg Thr Gly His Gly Gly Val Asn Gln Leu Gly
        10                  15                  20 ggg gtt ttt gtg aat gga cgg cca ctc ccg gat gta gtc cgc cag agg      568
Gly Val Phe Val Asn Gly Arg Pro Leu Pro Asp Val Val Arg Gln Arg
 25                  30                  35                  40 ata gtg gaa ctt gct cat caa ggt gtc agg ccc tgc gac atc tcc agg      616
Ile Val Glu Leu Ala His Gln Gly Val Arg Pro Cys Asp Ile Ser Arg
                45                  50                  55 cag ctt cgg gtc agc cat ggt tgt gtc agc aaa att ctt ggc agg tat      664
Gln Leu Arg Val Ser His Gly Cys Val Ser Lys Ile Leu Gly Arg Tyr
            60                  65                  70 tat gag aca gga agc atc aag cct ggg gta att gga gga tcc aaa cca      712
Tyr Glu Thr Gly Ser Ile Lys Pro Gly Val Ile Gly Gly Ser Lys Pro
        75                  80                  85 aag gtc gcc aca ccc aaa gtg gtg gaa aaa atc gct gaa tat aaa cgc      760
Lys Val Ala Thr Pro Lys Val Val Glu Lys Ile Ala Glu Tyr Lys Arg
 90                  95                 100 caa aat ccc acc atg ttt gcc tgg gag atc agg gac cgg ctg ctg gca      808
Gln Asn Pro Thr Met Phe Ala Trp Glu Ile Arg Asp Arg Leu Leu Ala
105                 110                 115                 120 gag cgg gtg tgt gac aat gac acc gtg cct agc gtc agt tcc atc aac      856
Glu Arg Val Cys Asp Asn Asp Thr Val Pro Ser Val Ser Ser Ile Asn
                125                 130                 135 agg atc atc cgg aca aaa gta cag cag cca ccc aac caa cca gtc cca      904
Arg Ile Ile Arg Thr Lys Val Gln Gln Pro Pro Asn Gln Pro Val Pro
            140                 145                 150 gct tcc agt cac agc ata gtg tcc act ggc tcc gtg acg cag gtg tcc      952
Ala Ser Ser His Ser Ile Val Ser Thr Gly Ser Val Thr Gln Val Ser
        155                 160                 165 tcg gtg agc acg gat tcg gcc ggc tcg tcg tac tcc atc agc ggc atc     1000
Ser Val Ser Thr Asp Ser Ala Gly Ser Ser Tyr Ser Ile Ser Gly Ile
170                 175                 180
```

```
ctg ggc atc acg tcc ccc agc gcc gac acc aac aag cgc aag aga gac      1048
Leu Gly Ile Thr Ser Pro Ser Ala Asp Thr Asn Lys Arg Lys Arg Asp
185                 190                 195                 200 gaa ggt att cag gag tct ccg gtg ccg aac ggc cac tcg ctt ccg ggc      1096
Glu Gly Ile Gln Glu Ser Pro Val Pro Asn Gly His Ser Leu Pro Gly
                205                 210                 215 aga gac ttc ctc cgg aag cag atg cgg gga gac ttg ttc aca cag cag      1144
Arg Asp Phe Leu Arg Lys Gln Met Arg Gly Asp Leu Phe Thr Gln Gln
            220                 225                 230 cag ctg gag gtg ctg gac cgc gtg ttt gag agg cag cac tac tca gac      1192
Gln Leu Glu Val Leu Asp Arg Val Phe Glu Arg Gln His Tyr Ser Asp
        235                 240                 245 atc ttc acc acc aca gag ccc atc aag ccc gag cag acc aca gag tat      1240
Ile Phe Thr Thr Thr Glu Pro Ile Lys Pro Glu Gln Thr Thr Glu Tyr
    250                 255                 260 tca gcc atg gcc tcg ctg gct ggt ggg ctg gac gac atg aag gcc aat      1288
Ser Ala Met Ala Ser Leu Ala Gly Gly Leu Asp Asp Met Lys Ala Asn
265                 270                 275                 280 ctg gcc agc ccc acc cct gct gac atc ggg agc agt gtg cca ggc ccg      1336
Leu Ala Ser Pro Thr Pro Ala Asp Ile Gly Ser Ser Val Pro Gly Pro
                285                 290                 295 cag tcc tac ccc att gtg aca ggc cgt gac ttg gcg agc acg acc ctc      1384
Gln Ser Tyr Pro Ile Val Thr Gly Arg Asp Leu Ala Ser Thr Thr Leu
            300                 305                 310 ccc ggg tac cct cca cac gtc ccc ccg gct gga cag ggc agc tac tca      1432
Pro Gly Tyr Pro Pro His Val Pro Pro Ala Gly Gln Gly Ser Tyr Ser
        315                 320                 325 gca ccg acg ctg aca ggg atg gtg cct ggg agt gag ttt tcc ggg agt      1480
Ala Pro Thr Leu Thr Gly Met Val Pro Gly Ser Glu Phe Ser Gly Ser
    330                 335                 340 ccc tac agc cac cct cag tat tcc tcg tac aac gac tcc tgg agg ttc      1528
Pro Tyr Ser His Pro Gln Tyr Ser Ser Tyr Asn Asp Ser Trp Arg Phe
345                 350                 355                 360 ccc aac ccg ggg ctg ctt ggc tcc ccc tac tat tat agc gct gcc gcc      1576
Pro Asn Pro Gly Leu Leu Gly Ser Pro Tyr Tyr Tyr Ser Ala Ala Ala
                365                 370                 375 cga gga gcc gcc cca cct gca gcc gcc act gcc tat gac cgt cac tga      1624
Arg Gly Ala Ala Pro Pro Ala Ala Ala Thr Ala Tyr Asp Arg His
            380                 385                 390 cccttggagc caggcgggca ccaaacactg atggcaccta ttgagggtga cagccaccca    1684
gccctcctga agatagccag agagcccatg agaccgtccc ccagcatccc ccacttgcct    1744
gaagctcccc tcttcctctc ttcctccagg gactctgggg ccctttggtg gggccgttgg    1804
acttctggat gcttgtctat ttctaaaagc caatctatga gcttctcccg atggccactg    1864
ggtctctgca aaccaataga ctgtcctgca ataaccgca gccccagccc agcctgcctg     1924
tcctccagct gtctgactat ccatccatca taaccacccc agcctgggaa ggagagcttg    1984
cttttgttgc ttcagcagca cccatgtaaa taccttcttg cttttctgtg ggcctgaagg    2044
tccgactgag aagactgctc cacccatgat gcatctcgca ctcttggtgc atcaccggac    2104
atcttagacc tatggcagag catcctctct gccctgggtg accctggcag gtgcgctcag    2164
agctgtcctc aagatggagg atgctgccct tgggccccag cctcctgctc atccctcctt    2224
ctttagtatc tttacgagga gtctcactgg gctggttgtg ctgcaggctc ccctgaggc     2284 ccctctccaa gaggagcaca ctttggggag atgtcctggt ttcctgcctc catttctctg    2344
ggaccgatgc agtatcagca gctctttttcc agatcaaaga actcaaagaa aactgtctgg   2404
gagattcctc agctactttt ccgaagcaga atgtcatccg aggtattgat tacattgtgg    2464
```

-continued

```
actttgaatg tgagggctgg atgggacgca ggagatcatc tgatcccagc caaggagggg      2524
cctgaggctc tccctactcc ctcagccct ggaacggtgt tttctgaggc atgcccaggt      2584
tcaggtcact tcggacacct gccatggaca cttcacccac cctccaggac cccagcaagt      2644
ggattctggg caagcctgtt ccggtgatgt agacaataat taacacagag gactttcccc      2704
cacacccaga tcacaaacag cctacagcca gaacttctga gcatcctctc ggggcagacc      2764
ctccccgtcc tcgtggagct tagcaggcag ctgggcatgg aggtgctggg gctggggcag      2824
atgcctaatt tcgcacaatg catgcccacc tgttgatcta aggggccgcg atggtcaggg      2884
ccacggccaa gggccacggg aacttggaga gggagcttgg agaactcact gtgggctagg      2944
gtggtcagag gaagccagca gggaagatct ggggggacaga ggaaggcctc ctgagggagg     3004
ggcaggagag cagtgaggag ctgctgtgtg acctgggagt gattttgaca tgggggtgcc      3064
aggtgccatc atctctttac ctgggggcctt aattccttgc atagtctctc ttgtcaagtc     3124
agaacagcca ggtagagccc ttgtccaaac ctgggctgaa tgacagtgat gagaggggcc     3184
ttggccttct taggtgacaa tgtcccccat atctgtatgt caccaggatg gcagagagcc      3244
agggcagaga gagactggac ttgggatcag caggccaggc aggtcttgtc ctggtcctgg      3304
ccacatgtct ttgctgtggg acctcagaca aaaccctgca cctctttgag ccttggctgc      3364
cttggtgcag cagggtcatc tgtagggcca ccccacagct cttcttcc cctcctctct      3424 ccagggagcc ggggctgtga gaggatcatc tgggcaggc cctccacttc caagcaagca      3484 gatggggtg gcacctgag gcccaataat atttggacca agtgggaaac aagaacactc      3544
ggaggggcgg gaatcagaag agcctggaaa aagacctagc ccaacttccc ttgtgggaaa      3604
ctgaggccca gcttggggaa ggccaggacc atgcagggag aaaaag              3650
```

<210> SEQ ID NO 14
<211> LENGTH: 230
<212> TYPE: DNA
<213> ORGANISM: Artificial Sequence
<220> FEATURE:
<223> OTHER INFORMATION: synthetic partial PAX5 coding sequence used to detect human PAX5 mRNA

<400> SEQUENCE: 14

```
gtccattcca tcaagtcctg aaaaatcaaa atggatttag agaaaaatta tccgactcct       60
cggaccagca ggacaggaca tggaggagtg aatcagcttg gggggttttt tgtgaatgga      120
cggccactcc cggatgtagt ccgccagagg atagtggaac ttgctcatca aggtgtcagg      180
ccctgcgaca tctccaggca gcttcgggtc agccatggtt gtgtcagcaa                 230
```

<210> SEQ ID NO 15
<211> LENGTH: 21
<212> TYPE: DNA
<213> ORGANISM: Artificial Sequence
<220> FEATURE:
<223> OTHER INFORMATION: synthetic methylation-sensitive PCR (MSP) primer PAX5mF1

<400> SEQUENCE: 15

```
tgaatcggag taaatcggaa c                                                 21
```

<210> SEQ ID NO 16
<211> LENGTH: 19
<212> TYPE: DNA
<213> ORGANISM: Artificial Sequence
<220> FEATURE:
<223> OTHER INFORMATION: synthetic methylation-sensitive PCR (MSP) primer PAX5mR1

```
<400> SEQUENCE: 16
cccgctactt aaacgaacg                                        19

<210> SEQ ID NO 17
<211> LENGTH: 23
<212> TYPE: DNA
<213> ORGANISM: Artificial Sequence
<220> FEATURE:
<223> OTHER INFORMATION: synthetic methylation-sensitive PCR (MSP)
      primer PAX5uF1

<400> SEQUENCE: 17
ggtgaattgg agtaaattgg aat                                   23

<210> SEQ ID NO 18
<211> LENGTH: 20
<212> TYPE: DNA
<213> ORGANISM: Artificial Sequence
<220> FEATURE:
<223> OTHER INFORMATION: synthetic methylation-sensitive PCR (MSP)
      primer PAX5uR1

<400> SEQUENCE: 18
ccccactact taaacaaaca                                       20

<210> SEQ ID NO 19
<211> LENGTH: 23
<212> TYPE: DNA
<213> ORGANISM: Artificial Sequence
<220> FEATURE:
<223> OTHER INFORMATION: synthetic methylation-sensitive PCR (MSP)
      primer PAX5mF3

<400> SEQUENCE: 19
gcgtatgttt aatagaagg tgc                                    23

<210> SEQ ID NO 20
<211> LENGTH: 20
<212> TYPE: DNA
<213> ORGANISM: Artificial Sequence
<220> FEATURE:
<223> OTHER INFORMATION: synthetic methylation-sensitive PCR (MSP)
      primer PAX5mR3

<400> SEQUENCE: 20
acttcaacct acgccgaacg                                       20

<210> SEQ ID NO 21
<211> LENGTH: 24
<212> TYPE: DNA
<213> ORGANISM: Artificial Sequence
<220> FEATURE:
<223> OTHER INFORMATION: synthetic methylation-sensitive PCR (MSP)
      primer PAX5uF3

<400> SEQUENCE: 21
agtgtatgtt ttaatagaag gtgt                                  24

<210> SEQ ID NO 22
<211> LENGTH: 21
<212> TYPE: DNA
<213> ORGANISM: Artificial Sequence
<220> FEATURE:
<223> OTHER INFORMATION: synthetic methylation-sensitive PCR (MSP)
      primer PAX5uR3
```

<400> SEQUENCE: 22
aacttcaacc tacaccaaac a        21

<210> SEQ ID NO 23
<211> LENGTH: 391
<212> TYPE: PRT
<213> ORGANISM: Homo sapiens
<220> FEATURE:
<223> OTHER INFORMATION: human transcription factor paired box 5 (PAX5, paired box homeotic gene 5), B-cell specific activation protein (BSAP) B-cell lineage specific activator, B-cell-specific transcription factor

<400> SEQUENCE: 23

```
Met Asp Leu Glu Lys Asn Tyr Pro Thr Pro Arg Thr Ser Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
        115                 120                 125

Val Pro Ser Val Ser Ser Ile Asn Arg Ile Ile Arg Thr Lys Val Gln
    130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
    210                 215                 220

Arg Gly Asp Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Ala Ser Pro Thr Pro Ala Asp
        275                 280                 285

Ile Gly Ser Ser Val Pro Gly Pro Gln Ser Tyr Pro Ile Val Thr Gly
    290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335
```

```
Pro Gly Ser Glu Phe Ser Gly Ser Pro Tyr Ser His Pro Gln Tyr Ser
            340                 345                 350

Ser Tyr Asn Asp Ser Trp Arg Phe Pro Asn Pro Gly Leu Leu Gly Ser
        355                 360                 365

Pro Tyr Tyr Tyr Ser Ala Ala Ala Arg Gly Ala Ala Pro Pro Ala Ala
370                 375                 380

Ala Thr Ala Tyr Asp Arg His
385                 390

<210> SEQ ID NO 24
<211> LENGTH: 307
<212> TYPE: DNA
<213> ORGANISM: Homo sapiens
<220> FEATURE:
<221> NAME/KEY: promoter
<222> LOCATION: (1)...(307)
<223> OTHER INFORMATION: human transcription factor paired box 5 (PAX5,
      paired box homeotic gene 5), B-cell specific activation protein
      (BSAP) B-cell lineage specific activator, B-cell-specific
      transcription factor promoter region -352 to -46

<400> SEQUENCE: 24
tgaatcggag taaaccggaa cgtcgcctcg gtgcctggca acactgccag cctttgcaac      60 cccctttcaaa agcacctgct tggccgagca gttaatttct tcaaaaacaa aaacccggcc    120
tgcgctcgtc taagcagcgg ggtttgcaca tggagatgtc acaggccccg cgcacagcgc    180
agagggccgc gaccccaag cgcatgtctt aatagaaggt gcggctggaa gacccgggct     240
cccgggctcc gcttcggtct gccccttccc gtaggtgcgc tggctagcgc ccggcgcagg    300
ctgaagc                                                              307

<210> SEQ ID NO 25
<211> LENGTH: 89
<212> TYPE: DNA
<213> ORGANISM: Artificial Sequence
<220> FEATURE:
<223> OTHER INFORMATION: synthetic PAX5 CpG island partial bisulfite
      genomic sequencing (BGS) region

<400> SEQUENCE: 25
tcggtttgcg ctcgtctaag cagcggggtt tgcacatgga gatgtcacag gccccgcgca     60
cagcgcagag ggccgcgacc cccaagcgc                                       89

<210> SEQ ID NO 26
<211> LENGTH: 105
<212> TYPE: DNA
<213> ORGANISM: Artificial Sequence
<220> FEATURE:
<223> OTHER INFORMATION: synthetic PAX5 CpG island methylation specific
      PCR (MSP) region, positions -248 to -144

<400> SEQUENCE: 26
aaacaaaaac ccggcctgcg ctcgtctaag cagcggggtt tgcacatgga gatgtcacag     60
gccccgcgca cagcgcagag ggccgcgacc cccaagcgca tgtct                    105

<210> SEQ ID NO 27
<211> LENGTH: 180
<212> TYPE: DNA
<213> ORGANISM: Artificial Sequence
<220> FEATURE:
<223> OTHER INFORMATION: synthetic PAX5 CpG island bisulfite genomic
      sequencing (BGS) region, positions -292 to -132
```

```
<400> SEQUENCE: 27
ccctttcaaa agcacctgct tggccgagca gttaatttct tcaaaaacaa aaacccggcc      60
tgcgctcgtc taagcagcgg ggtttgcaca tggagatgtc acaggcccccg cgcacagcgc    120 agagggccgc gacccccaag cgcatgtctt aatagaaggt gcggctggaa gacccgggct    180
```